United States Patent [19]

Barclay

[11] Patent Number: 5,656,319
[45] Date of Patent: Aug. 12, 1997

[54] FOOD PRODUCT WITH HIGH CONCENTRATIONS OF OMEGA-3 HIGHLY UNSATURATED FATTY ACIDS

[75] Inventor: William R. Barclay, Boulder, Colo.

[73] Assignee: Omega Tech Inc., Boulder, Colo.

[21] Appl. No.: 292,736

[22] Filed: Aug. 18, 1994

Related U.S. Application Data

[62] Division of Ser. No. 911,760, Jul. 10, 1992, Pat. No. 5,340,594, which is a division of Ser. No. 580,778, Sep. 11, 1990, Pat. No. 5,130,242, which is a continuation-in-part of Ser. No. 439,093, Nov. 17, 1989, abandoned, which is a continuation-in-part of Ser. No. 241,410, Sep. 7, 1988, abandoned.

[51] Int. Cl.$^6$ ................................................ A23L 1/00
[52] U.S. Cl. .................... 426/574; 426/2; 426/49; 426/53; 426/614; 426/643; 426/644; 426/645; 426/602; 435/134; 435/243; 435/946
[58] Field of Search ............................ 426/49, 53, 2; 435/134, 243, 946

[56] References Cited

U.S. PATENT DOCUMENTS 5,012,761  5/1991  Oh ............................................. 119/6.8
5,415,879  5/1995  Oh ................................................ 426/2

FOREIGN PATENT DOCUMENTS 60-105471  10/1985  Japan .

OTHER PUBLICATIONS

Couch et al., 1973, *Lipids*, 8(7):385–392.
Cruickshank, 1934, "Studies in Fat Metabolism in the Fowl" in *Biochem. J.*, 28:965–977.
Fisher et al., 1957, *J. Nutr.*, 63:119–129.
Lipstein et al., "The Nutritional and Economic Value of Algae for Poultry" in *Algae Biomass*, G. Shelef and C.J. Soeder, eds., Elsevier/North–Holland Biomedical Press, 1980, pp. 667–685.
Lipstein et al., 1980, *Br. Poultry Sci.*, 21:9–21.
Murty et al., 1961, *J. Nutrition*, 75:287–294.
Navarro et al., 1972, *J. Sci. Fd. Agric.*, 23:1287–1292.
Reiser, 1951, *J. Nutrition*, 44:159–175.

*Primary Examiner*—Anthony J. Weier
*Attorney, Agent, or Firm*—Sheridan Ross P.C.

[57] ABSTRACT

A process for the heterotrophic or predominantly heterotrophic production of whole-celled or extracted microbial products with a high concentration of omega-3 highly unsaturated fatty acids, producible in an aerobic culture under controlled conditions using biologically pure cultures of heterotrophic single-celled fungi microorganisms of the order Thraustochytriales. The harvested whole-cell microbial product can be added to processed foods as a nutritional supplement, or to fish and animal feeds to enhance the omega-3 highly unsaturated fatty acid content of products produced from these animals. The lipids containing these fatty acids can also be extracted and used in nutritional, pharmaceutical and industrial applications.

8 Claims, 9 Drawing Sheets

FOOD PRODUCT WITH HIGH CONCENTRATIONS OF OMEGA-3 HIGHLY UNSATURATED FATTY ACIDS

CROSS-REFERENCE TO RELATED APPLICATIONS

This application is a divisional of U.S. patent application Ser. No. 07/911,760, filed Jul. 10, 1992, and issued as U.S. Pat. No. 5,340,594 which is a divisional of application Ser. No. 07/580,778, filed Sep. 11, 1990 and issued on Jul. 14, 1992 as U.S. Pat. No. 5,130,242, which is a continuation-in-part of commonly assigned U.S. patent application Ser. No. 07/439,093, filed Nov. 17, 1989, now abandoned and entitled "Process for Heterotrophic Production of Microbial Products with High Concentrations of Omega-3 Highly Unsaturated Fatty Acids" which is incorporated herein in its entirety by reference and is a continuation-in-part of U.S. patent application Ser. No. 07/241,410, filed Sep. 7, 1988, and entitled "Process for Heterotrophic Production of Microbial Products with High Concentrations of Omega-3 Highly Unsaturated Fatty Acids" which was previously expressly abandoned.

FIELD OF THE INVENTION

The field of this invention relates to heterotrophic organisms and a process for culturing them for the production of lipids with high concentrations of omega-3 highly unsaturated fatty acids (HUFA) suitable for human and animal consumption as food additives or for use in pharmaceutical and industrial products.

BACKGROUND OF THE INVENTION

Omega-3 highly unsaturated fatty acids are of significant commercial interest in that they have been recently recognized as important dietary compounds for preventing arteriosclerosis and coronary heart disease, for alleviating inflammatory conditions and for retarding the growth of tumor cells. These beneficial effects are a result both of omega-3 highly unsaturated fatty acids causing competitive inhibition of compounds produced from omega-6 fatty acids, and from beneficial compounds produced directly from the omega-3 highly unsaturated fatty acids themselves (Simopoulos et al., 1986). Omega-6 fatty acids are the predominant highly unsaturated fatty acids found in plants and animals. Currently the only commercially available dietary source of omega-3 highly unsaturated fatty acids is from certain fish oils which can contain up to 20–30% of these fatty acids. The beneficial effects of these fatty acids can be obtained by eating fish several times a week or by daily intake of concentrated fish oil. Consequently large quantities of fish oil are processed and encapsulated each year for sale as a dietary supplement.

However, there are several significant problems with these fish oil supplements. First, they can contain high levels of fat-soluble vitamins that are found naturally in fish oils. When ingested, these vitamins are stored and metabolized in fat in the human body rather than excreted in urine. High doses of these vitamins can be unsafe, leading to kidney problems or blindness and several U.S. medical associations have cautioned against using capsule supplements rather than real fish. Secondly, fish oils contain up to 80% of saturated and omega-6 fatty acids, both of which can have deleterious health effects. Additionally, fish oils have a strong fishy taste and odor, and as such cannot be added to processed foods as a food additive, without negatively affecting the taste of the food product. Moreover, the isolation of pure omega-3 highly unsaturated fatty acids from this mixture is an involved and expensive process resulting in very high prices ($200–$1000/g) for pure forms of these fatty acids (Sigma Chemical Co., 1988; CalBiochem Co., 1987).

The natural source of omega-3 highly unsaturated fatty acids in fish oil is algae. These highly unsaturated fatty acids are important components of photosynthetic membranes. Omega-3 highly unsaturated fatty acids accumulate in the food chain and are eventually incorporated in fish oils. Bacteria and yeast are not able to synthesize omega-3 highly unsaturated fatty acids and only a few fungi are known which can produce minor and trace amounts of omega-3 highly unsaturated fatty acids (Weete, 1980; Wassef, 1977; Erwin, 1973).

Algae have been grown in outdoor cultivation ponds for the photoautotrophic production of a wide variety of products including omega-3 highly unsaturated fatty acid containing biomass. For example, U.S. Pat. No. 4,341,038 describes a method for the photosynthetic production of oils from algae, and U.S. Pat. No. 4,615,839 describes a process for concentrating eicosapentaenoic acid (EPA) (one of the omega-3 highly unsaturated fatty acids) produced photosynthetically by strains of the green alga Chlorella. Photoautotrophy is the process whereby cells utilize the process of photosynthesis to construct organic compounds from $CO_2$ and water, while using light as an energy source. Since sunlight is the driving force for this type of production system, algal cultivation ponds require large amounts of surface area (land) to be economically viable. Due to their large size, these systems cannot be economically covered, because of high costs and technical problems, and because even transparent covers tend to block a significant amount of the sunlight. Therefore, these production systems are not axenic, and are difficult to maintain as monocultures. This is especially critical if the cultures need to be manipulated or stressed (e.g. nitrogen limited) to induce production of the desired product. Typically, it is during these periods of stress, when the cells are only producing product and are not multiplying, that contaminants can readily invade the cultures. Thus, in most cases, the biomass produced is not desirable as a food additive for human consumption without employing expensive extraction procedures to recover the lipids. Additionally, photosynthetic production of algae in outdoor systems is very costly, since cultures must be maintained at low densities (1–2 g/l) to prevent light limitation of the culture. Consequently, large volumes of water must be processed to recover small quantities of algae, and since the algal cells are very tiny, expensive harvesting processes must also be employed.

Mixotrophy is an alternative mode of production whereby certain strains of algae carry on photosynthesis with light as a necessary energy source but additionally use organic compounds supplied in the medium. Higher densities can be achieved by mixotrophic production and the cultures can be maintained in closed reactors for axenic production. U.S. Pat. Nos. 3,444,647 and 3,316,674 describe processes for the mixotrophic production of algae. However, because of the need to supply light to the culture, production reactors of this type are very expensive to build and operate, and culture densities are still very limited.

An additional problem with the cultivation of algae for omega-3 highly unsaturated fatty acid production, is that even though omega-3 highly unsaturated fatty acids comprise 20–40% of some strains total fatty acids, the total fatty acid content of these algae is generally very low, ranging from 5–10% of ash-free dry weight. In order to increase the fatty acid content of the cells, they must undergo a period of nitrogen limitation which stimulates the production of lipids. However, of all the strains noted to date in the literature, and over 60 strains evaluated by the inventor, all exhibit a marked decrease in omega-3 highly unsaturated fatty acids as a percentage of total fatty acids, when undergoing nitrogen limitation (Erwin, 1973; Pohl & Zurheide, 1979).

With respect to economics and to utilizing omega-3 highly unsaturated fatty acids as a food additive, it would be desirable to produce these fatty acids in a heterotrophic culture. Heterotrophy is the capacity for sustained and continuous growth and cell division in the dark in which both energy and cell carbon are obtained solely from the metabolism of an organic substrate(s). Since light does not need to be supplied to a heterotrophic culture, the cultures can be grown at very high densities in closed reactors. Heterotrophic organisms are those which obtain energy and cell carbon from organic substrates, and are able to grow in the dark. Heterotrophic conditions are those conditions that permit the growth of heterotrophic organisms, whether light is present or not. However, the vast majority of algae are predominantly photoautotrophic, and only a few types of heterotrophic algae are known. U.S. Pat. Nos. 3,142,135 and 3,882,635 describe processes for the heterotrophic production of protein and pigments from algae such as Chlorella, Spongiococcum, and Prototheca. However these genera and others that have been documented to grow very well heterotrophically (e.g. Scenedesmus), do not produce omega-3 highly unsaturated fatty acids (Erwin, 1973). The very few heterotrophic algae known to produce any omega-3 highly unsaturated fatty acids (e.g., apochlorotic diatoms or apochlorotic dinoflagellates) generally grow slowly and produce low amounts of omega-3 highly unsaturated fatty acids as a percentage of ash-free dry weight (Harrington and Holtz, 1968; Tornabene et al., 1974).

A few higher fungi are known to produce omega-3 highly unsaturated fatty acids, but they comprise only a very small fraction of the total fatty acids in the cells (Erwin, 1973; Wassef, 1977; Weete, 1980). As such, they would not be good candidates for commercial production of omega-3 highly unsaturated fatty acids. For example, Yamada et al. (1987) recently reported on the cultivation of several species of the fungus, Mortierella, (isolated from soils) for the production of the omega-6 fatty acid, arachidonic acid. These fungi also produce small amounts of omega-3 eicosapentaenoic acid along with the arachidonic acid when grown at low temperatures (5°–24° C.). However, the resulting eicosapentaenoic acid content was only 2.6% of the dry weight of the cells, and the low temperatures necessary to stimulate production of this fatty acid in these species would result in greatly decreased productivities (and economic potential) of the cultivation system. Some single-celled members of the order Thraustochytriales are also known to produce omega-3 highly unsaturated fatty acids (Ellenbogen, 1969, Wassef, 1977; Weete, 1980; Findlay et. al., 1986) but they are known to be difficult to culture. Sparrow (1960) noted that the minuteness and simple nature of the thalli of the family Thraustochytriaceae (order Thraustochytriales) make them exceedingly difficult to propagate. Additional reasons for this difficulty have been outlined by Emerson (1950) and summarized by Schneider (1976): "1) these fungi consist of very small thalli of only one or a few cells, which generally grow very slowly in culture, and are very sensitive to environmental perturbation; 2) they are generally saprophytes, or parasites with very specialized nutritional and environmental demands; and 3) in pure culture they generally exhibit restricted growth, with vegetative growth terminating after a few generations." (Although some prior art classifies the thraustochytrids as fungi, the most recent consensus is that they should be classified as algae, see discussion below.)

As a result little attention has been paid to the numerous orders of these microorganisms, and those studies that have been conducted, have been predominantly carried out with a taxonomic or ecological focus. For example, even though the simple fatty acid distribution of several members of the order Thraustochytriales has been reported from a taxonomic perspective (Ellenbogen, 1969); Findlay et al., 1986), no one has ever reported their total fatty acid content or lipid content as percent dry weight. Unless data on the total lipid content is available, one cannot evaluate an organism's potential for use in the production of any type of fatty acid. For example, the omega-3 highly unsaturated fatty acid content of the lipids of some marine macroalgae (seaweeds) is reported to be very high, up to 51% of total fatty acids (Pohl & Zurheide, 1979). However, the lipid content of macroalgae is typically very low, only 1–2% of cellular dry weight (Ryther, 1983). Therefore, despite the reported high content of omega-3 highly unsaturated fatty acids in the fatty acids of macroalgae, they would be considered to be very poor candidate organisms for the production of omega-3 highly unsaturated fatty acids. Despite a diligent search by the inventor, no reports of simple proximate analysis (% protein, carbohydrate and lipid) of the Thraustochytriales has been found, nor has anyone reported attempts to cultivate these species for purposes other than laboratory studies of their taxonomy, physiology or ecology. Additionally, many of the strains of these microorganisms have been isolated by simple pollen baiting techniques (e.g., Gaertner, 1968). Pollen baiting techniques are very specific for members of the Thraustochytriales, but do not select for any characteristics which may be desirable for large scale cultivation Of microorganisms.

Thus, until the present invention, there have been no known heterotrophic organisms suitable for culture that produce practical levels of omega-3 highly unsaturated fatty acids and such organisms have been thought to be very rare in the natural environment.

BRIEF SUMMARY OF THE INVENTION

The present invention is directed toward a food product with a high concentration of omega-3 highly unsaturated fatty acids (HUFAs) which includes microorganisms characterized by having a high concentration of fatty acids of which a high percentage are omega-3 highly unsaturated fatty acids. In addition or alternatively, the food product can include omega-3 HUFAs extracted from the microorganisms. Specifically, the microorganisms are Thraustochytriales, namely, Thraustochytrium or Schizochytrium. The microorganisms or extracted omega-3 HUFAs are incorporated with additional food material which may be either animal food or human food. The food product of the present invention may have the bioavailability of the omega-3 HUFAs contained therein increased by lysing the cells of the microorganisms. The food product may also be extruded. In order to prevent degradation of the omega-3 HUFAs, the food product may be packaged under non-oxidizing conditions or may further comprise an antioxidant.

Another embodiment of the present invention relates to a method of raising an animal comprising feeding the animal Thraustochytriales or omega-3 HUFAs extracted therefrom. Animals raised by the method of the present invention include poultry, cattle, swine and seafood, which includes fish, shrimp and shellfish. The omega-3 HUFAs are incorporated into the flesh, eggs and other products of these animals which are consumed by humans.

Omega-3 HUFAs may be consumed as the whole cell microbial product, the extracted omega-3 HUFA product, or the animal or animal product incorporating omega-3 HUFAs. Increased intake of omega-3 HUFAs produced in accordance with the present invention by humans is effective in preventing or treating cardiovascular diseases, inflammatory and/or immunological diseases, and cancer.

Yet another embodiment of the present invention is a method of producing omega-3 HUFAs which comprises culturing Thraustochytriales in a medium with a source of organic carbon and assimilable nitrogen. Preferably, the source of organic carbon and assimilable nitrogen comprises ground grain. The method further comprises culturing Thraustochytriales consisting of Thraustochytrium, Schizochytrium, or mixtures thereof under nutrient-limited or nitrogen-limited conditions for an effective amount of time, preferably about 6 to about 24 hours, and harvesting the Thraustochytriales during the period of nitrogen limitation in order to increase the concentration of omega-3 HUFAs in the microorganisms. The method further comprises adding an antioxidant compound selected from the group consisting of BHT, BHA, TBHQ, ethoxyquin, beta-carotene, vitamin E and vitamin C during post-harvest processing in order to prevent degradation of the omega-3 HUFAs. The method further comprises stressing the microorganisms with low temperatures during culturing, maintaining a high dissolved oxygen concentration in the medium during culturing, and adding to the medium effective amounts of phosphorous and a microbial growth factor (yeast extract or corn steep liquor) to provide sustained growth of the microorganisms. The present method further includes culturing unicellular microorganisms having the identifying characteristics of ATCC Nos. 20888, 20889, 20890, 20891, 20892 and mutant strains derived therefrom. Omega-3 HUFAs produced by the method can then be separated from the lipids extracted from the microorganisms by fractional crystallization which comprises rupturing the microorganism cells, extracting the lipid mixture from the ruptured cells with a solvent, hydrolyzing the lipid mixture, removing non-saponifiable compounds and cold-crystallizing the non-HUFAs in the lipid mixture.

A further embodiment of the present invention is a method for selecting unicellular, aquatic microorganisms capable of heterotrophic growth and capable of producing omega-3 HUFAs comprising selecting microorganisms of a size between about 1 μm and 25 μm from a small population of microorganisms collected from naturally occuring shallow saline habitats, culturing the microorganisms in a medium comprising organic carbon, assimilable nitrogen, assimilable phosphorous and a microbial growth factor under heterotrophic conditions, and selecting clear, white, orange, or red-colored non-filamentous colonies having rough or textured surfaces.

DETAILED DESCRIPTION OF THE PREFERRED EMBODIMENTS

For purposes of definition throughout the application, it is understood herein that a fatty acid is an aliphatic monocarboxylic acid. Lipids are understood to be fats or oils including the glyceride esters of fatty acids along with associated phosphatides, sterols, alcohols, hydrocarbons, ketones, and related compounds.

A commonly employed shorthand system is used in this specification to denote the structure of the fatty acids (e.g., Weete, 1980). This system uses the letter "C" accompanied by a number denoting the number of carbons in the hydrocarbon chain, followed by a colon and a number indicating the number of double bonds, i.e., C20:5, eicosapentaenoic acid. Fatty acids are numbered starting at the carboxy carbon. Position of the double bonds is indicated by adding the Greek letter delta ($\Delta$) followed by the carbon number of the double bond; i.e., C20:5omega-3$\Delta^{5,8,11,14,17}$. The "omega" notation is a shorthand system for unsaturated fatty acids whereby numbering from the carboxy-terminal carbon is used. For convenience, w3 will be used to symbolize "omega-3," especially when using the numerical shorthand nomenclature discribed herein. Omega-3 highly unsaturated fatty acids are understood to be polyethylenic fatty acids in which the ultimate ethylenic bond is 3 carbons from and including the terminal methyl group of the fatty acid. Thus, the complete nomenclature for eicosapentaenoic acid, an omega-3 highly unsaturated fatty acid, would be C20:5w3$\Delta^{5,8,11,14,17}$. For the sake of brevity, the double bond locations ($\Delta^{5,8,11,14,17}$) will be omitted. Eicosapentaenoic acid is then designated C20:5w3, Docosapentaenoic acid (C22:5w3$\Delta^{7,10,13,16,19}$) is C22:5w3, and Docosahexaenoic acid (C22:6w3$\Delta^{4,7,10,13,16,19}$) is C22:6w3. The nomenclature "highly unsaturated fatty acid" means a fatty acid with 4 or more double bonds. "Saturated fatty acid" means a fatty acid with 1 to 3 double bonds.

A collection and screening process was developed by the inventor to readily isolate many strains of microorganisms with the following combination of economically desirable characteristics for the production of omega-3 highly unsaturated fatty acids: 1) capable of heterotrophic growth; 2) high content of omega-3 highly unsaturated fatty acids; 3) unicellular; 4) preferably low content of saturated and omega-6 highly unsaturated fatty acids; 5) preferably nonpigmented, white or essentially colorless cells; 6) preferably thermotolerant (ability to grow at temperatures above 30° C.); and 7) preferably euryhaline (able to grow over a wide range of Salinities, but especially at low salinities).

Collection, isolation and selection of large numbers of suitable heterotrophic strains can be accomplished by the following method. Suitable water samples and organisms typically can be collected from shallow, saline habitats which preferably undergo a wide range of temperature and salinity variation. These habitats include marine tide pools, estuaries and inland saline ponds, springs, playas and lakes. Specific examples of these collection sites are: 1) saline warm springs such as those located along the Colorado river in Glenwood Springs, Colo., or along the western edge of the Stansbury Mountains, Utah; 2) playas such as Goshen playa located near Goshen, Utah; 3) marine tide pools such as those located in the Bird Rocks area of La Jolla, Calif.; and 4) estuaries, such as Tiajuana estuary, San Diego County, Calif. Special effort should be made to include some of the living plant matter and naturally occurring detritus (decaying plant and animal matter) along with the water sample. The sample can then be refrigerated until return to the laboratory. Sampling error is minimized if the water sample is shaken for 15–30 seconds, prior to pipetting or pouring a portion, for example, 1–10 ml, into a filter unit. The filter unit includes 2 types of filters: 1) on top, a sterile Whatman #4 filter (Trademark, Whatman Inc., Clifton, N.J.); and 2) underneath the Whatman filter, a polycarbonate filter with 1.0 μm pore size. The purpose of the first (top) filter is to remove all particulate matter greater than about 25 μm, generally allowing only unicellular type material to pass onto the 1.0 µm polycarbonate filter. The first filter greatly reduces the number of mold colonies that subsequently develop upon incubation of the polycarbonate filter at elevated temperatures, thereby enhancing the opportunities for other colonies to develop. Mold spores are very numerous in coastal and inland saline waters, and mold colonies can quickly cover an agar plate unless screened out. The 1.0 µm size of the polycarbonate filter is chosen to allow many of the bacteria to pass on through into the filtrate. The purpose of using a sandwich filter design is to select for unicellular organisms at least a portion of whose cells range in diameter from about 1 µm to about 25 µm in size (organisms which could potentially be grown easily in a fermenter system for production on a large scale). Extensive growth of these unicellular organisms can be encouraged by incubation of the polycarbonate filter on an agar plate. Competition between organisms growing on the filter facilitates the isolation of competitive, robust strains of single-celled microorganisms. Unicellular aquatic microorganisms selected by the foregoing method display a range of cell size depending on growth conditions and stage of reproductive cycle. Most cells in culture have diameters in the range from about 1 µm to about 25 µm; however, cells (thalli and sporangia) in the cultures can be found that have larger diameters (depending on the strain) up to about 60 µm.

After filtration, the polycarbonate filter can be placed on an agar plate containing saline media containing a source of organic carbon such as carbohydrate including glucose, various starches, molasses, ground corn and the like, a source of assimilable organic or inorganic nitrogen such as nitrate, urea, ammonium salts, amino acids, microbial growth factors included in one or more of yeast extract, vitamins, and corn steep liquor, a source of assimilable organic or inorganic phosphorous, and a pH buffer such as bicarbonate. Microbial growth factors are currently unspecified compounds which enhance heterotrophic growth of unicellular microorganisms, including fungi and algae. The agar plates can be incubated in the dark at 25°–35° C. (30° C. is preferred) and after 2–4 days numerous colonies will have appeared on the filter. Recovery of 1–5 colonies/plate of the desired organism is not uncommon. Yeast colonies are distinguishable either by color (they frequently are pink) or by their morphology. Yeast colonies are smooth whereas the desired organisms form in colonies with rough or textured surfaces. Individual cells of the desired organism can be seen through a dissecting microscope at the colony borders, whereas yeast cells are not distinguishable, due to their smaller size. Mold and higher fungi colonies are distinguishable from the desired organisms because they are filamentous, whereas the desired organisms are non-filamentous. Clear or white-colored colonies can be picked from the plates and restreaked on a new plate of similar media composition. While most of the desired organisms are clear or white-colored, some are orange or red-colored due to the presence of xanthophyll pigments and are also suitable for selection and restreaking. The new plate can be incubated under similar conditions, preferably at 30° C. and single colonies picked after a 2–4 day incubation period. Single colonies can then be picked and placed in, for example, 50 ml of liquid medium containing the same organic enrichments (minus agar) as in the agar plates. These cultures can be incubated for 2–4 days at 30° C. with aeration, for example, on a rotary shaker table (100–200 rpm.). When the cultures appear to reach maximal density, 20–40 ml of the culture can then be harvested by centrifugation or other suitable method and preserved, as by lyophilization. The sample can then be analyzed by standard, well-known techniques including gas chromatography techniques to identify the fatty acid content of the strain. Those strains with omega-3 highly unsaturated fatty acids can thereby be identified and cultures of these strains maintained for further screening.

Promising strains can be screened for temperature tolerance by inoculating the strains into 250 ml shaker flasks containing 50 ml of culture media. These cultures are then incubated for 2 days on the shaker table over any desired temperature range from most practically between 27°–48° C., one culture at each 3° C. interval. Production can be quantified as the total amount of fatty acids produced per ml of culture medium. Total fatty acids can be quantified by gas chromatography as described above. A similar process can also be employed to screen for salinity tolerance. For salinity tolerance a range of salinities yielding conductivities from 5–40 mmho/cm is adequate for most purposes. Screening for the ability to utilize a variety of carbon and nitrogen sources can also be conducted employing the procedure outlined above. The carbon and nitrogen sources were evaluated herein at concentrations of 5 g/l. Carbon sources evaluated were: glucose, corn starch, ground corn, potato starch, wheat starch, and molasses. Nitrogen sources evaluated were: nitrate, urea, ammonium, amino acids, protein hydrolysate, corn steep liquor, tryptone, peptone, or casein. Other carbon and nitrogen sources can be used, the choice being open to those of ordinary skill in the art, based on criteria of significance to the user.

It has been unexpectedly found that species/strains from the genus Thrausochytrium can directly ferment ground, unhydrolyzed grain to produce omega-3 HUFAs. This process is advantageous over conventional fermentation processes because such grains are typically inexpensive sources of carbon and nitrogen. Moreover, practice of this process has no detrimental effects on the beneficial characteristics of the algae, such as levels of omega-3 HUFAs.

The present process using direct fermentation of grains is useful for any type of grain, including without limitation, corn, sorghum, rice, wheat, oats, rye and millet. There are no limitations on the grind size of the grain. However, it is preferable to use at least coarsely ground grain and more preferably, grain ground to a flour-like consistency. This process further includes alternative use of unhydrolyzed corn syrup or agricultural/fermentation by-products such as stillage, a waste product in corn to alcohol fermentations, as an inexpensive carbon/nitrogen source.

In another preferred process, it has been found that omega-3 HUFAs can be produced by Thraustochytrium or Schizochytrium by fermentation of above-described grains and waste products which have been hydrolyzed. Such grains and waste products can be hydrolyzed by any method known in the art, such as acid hydrolysis or enzymatic hydrolysis. A further embodiment is a mixed hydrolysis treatment. In this procedure, the ground grain is first partially hydrolyzed under mild acid conditions according to any mild acid treatment method known in the art. Subsequently, the partially hydrolyzed ground grain is further hydrolyzed by an enzymatic process according to any enzymatic process known in the art. In this preferred process, enzymes such as amylase, amyloglucosidase, alpha or beta glucosidase, or a mixture of these enzymes are used. The resulting hydrolyzed product is then used as a carbon and nitrogen source in the present invention.

Using the collection and screening process outlined above, strains of unicellular fungi and algae can be isolated which have omega-3 highly unsaturated fatty acid contents up to 32% total cellular ash-free dry weight (afdw), and which exhibit growth over a temperature range from 15°–48° C. and grow in a very low salinity culture medium. Many of the very high omega-3 strains are very slow growers. Stains which have been isolated by the method outlined above, and which exhibit rapid growth, good production and high omega-3 highly unsaturated fatty acid content, have omega-3 unsaturated fatty acid contents up to approximately 10% afdw.

Growth of the strains by the invention process can be effected at any temperature conducive to satisfactory growth of the strains, for example, between about 15° C. and 48° C., and preferably between 25°–36° C. The culture medium typically becomes more alkaline during the fermentation if pH is not controlled by acid addition or buffers. The strains will grow over a pH range from 4.0–11.0 with a preferable range of about 5.5–8.5.

When growth is carried out in large vessels and tanks, it is preferable to produce a vegetative inoculum in a nutrient broth culture by inoculating this broth culture with an aliquot from a slant culture or culture preserved at –70° C. employing the cryoprotectants dimethylsulfoxide (DMSO) or glycerol. When a young, active vegetative inoculum has then been secured, it can be transferred aseptically to larger production tanks or fermenters. The medium in which the vegetative inoculum is produced can be the same as, or different from, that utilized for the large scale production of cells, so long as a good growth of the strain is obtained.

The inventor found that single-celled strains of the order Thraustochytriales (containing omega-3 fatty acids) isolated and screened by the process outlined above, generally exhibited restricted growth, with vegetative growth terminating after a few generations as predicted by Emerson (1950) and Schneider (1976). However, the inventor found that by maintaining relatively high concentrations of phosphorous (e.g., $KH_2PO_4$>0.2 g/l) and/or adding a nutritional supplement (source of fungal growth factors) such as yeast extract or corn steep liquor (greater than 0.2 g/l), continuously growing cultures of these unicellular fungi could be maintained. The ability to maintain growth for more than 2–3 generations in liquid culture is termed herein sustained growth. As a group, strains in the genus Thraustochytrium appear to respond more favorably to phosphate additions than those in the genus Schizochytrium, which appear to need less phosphate. In terms of nutritional supplements supplying fungal growth factors, corn steep liquor can be substituted for the yeast extract, and with some strains, has even a more enhanced effect for allowing the strains to achieve high densities in culture. The corn steep liquor and yeast extract contain one or more growth factors necessary for growth of the cells. While the growth factor(s) is not presently defined, it is a component of yeast extract and corn steep liquor, and either of these well-known nutritional supplements are satisfactory. Carbon conversion efficiencies close to 50% (g cell dry weight produced/100 g organic carbon added to culture medium) can easily be achieved employing this process.

A microbial product high in protein and high in omega-3 highly unsaturated fatty acids can be produced by harvesting the cells in the exponential phase of growth. If a product significantly higher in lipids and omega-3 highly unsaturated fatty acids is desired, the culture can be manipulated to become nutrient limited, preferably, nitrogen limited for a suitable time, preferably in the range from 6 to 24 hours. The cultures can be transferred to a nitrogen-free medium or, preferably, the initial nitrogen content of the growth medium can be provided such that nitrogen becomes depleted late in the exponential phase. Nitrogen limitation stimulates total lipid production while maintaining high levels of omega-3 highly unsaturated fatty acids as long as the induction period is kept short, usually 6–24 hours. This phase of the culture, when the culture population has achieved its maximum cell density, is known as the stationary phase. Length of the induction period can be manipulated by raising or lowering temperature, depending on the strain employed. Additionally, the cells can be cultured on a continuous basis in a medium with a high carbon-to-nitrogen ratio, enabling continuous production of high lipid content (and high omega-3 content) cellular biomass. The unicellular strains of heterotrophic microorganisms isolated by the screening procedure outlined above, tend to have high concentrations of three omega-3 highly unsaturated fatty acids: C20:5w3, C22:5w3 and C22:6w3 and very low concentration of C20:4w6. The ratios of these fatty acids can vary depending on culture conditions and the strains employed. Ratios of C20:5w3 to C22:6w3 can run from about 1:1 to 1:30. Ratios of C22:5w3 to C22:6w3 can run from 1:12 to only trace amounts of C22:5w3. In the strains that lack C22:5w3, the C20:5w3 to C22:6w3 ratios can run from about 1:1 to 1:10. An additional highly unsaturated fatty acid, C22:5w6 is produced by some of the strains, including all of the prior art strains (up to a ratio of 1:4 with the C22:6w3 fatty acid). However, C22:5w6 fatty acid is considered undesirable as a dietary fatty acid because it can retroconvert to the C20:4w6 fatty acid. The screening procedure outlined in this invention, however, facilitates the isolation of some strains that contain no (or less than 1%) omega-6 highly unsaturated fatty acids (C20:4w6 or C22:5w6).

HUFAs in microbial products, such as those produced by the present process, when exposed to oxidizing conditions can be converted to less desirable unsaturated fatty acids or to saturated fatty acids. However, saturation of omega-3 HUFAs can be reduced or prevented by the introduction of synthetic antioxidants or naturally-occurring antioxidants, such as beta-carotene, vitamin E and vitamin C, into the microbial products.

Synthetic antioxidants, such as BHT, BHA, TBHQ or ethoxyquin, or natural antioxidants such as tocopherols, can be incorporated into the food or feed products by adding them to the products during processing of the cells after harvest. The amount of antioxidants incorporated in this manner depends, for example, on subsequent use requirements, such as product formulation, packaging methods, and desired shelf life.

Concentrations of naturally-occurring antioxidants can be manipulated by harvesting a fermentation in stationary phase rather than during exponential growth, by stressing a fermentation with low temperature, and/or by maintaining a high dissolved oxygen concentration in the medium. Additionally, concentrations of naturally occurring antioxidants can be controlled by varying culture conditions such as temperature, salinity, and nutrient concentrations. Additionally, biosynthetic precursors to vitamin E, such as L-tyrosine or L-phenylalanine, can be incorporated into fermentation medium for uptake and subsequent conversion to vitamin E. Alternatively, compounds which act synergistically with antioxidants to prevent oxidation (e.g., ascorbic acid, citric acid, phosphoric acid) can be added to the fermentation for uptake by the cells prior to harvest. Additionally, concentrations of trace metals, particularly those that exist in two or more valency states, and that possess suitable oxidation-reduction potential (e.g., copper, iron, manganese, cobalt, nickel) should be maintained at the minimum needed for optimum growth to minimize their potential for causing autooxidation of the HUFAs in the processed cells.

Other products that can be extracted from the harvested cellular biomass include: protein, carbohydrate, sterols, carotenoids, xanthophylls, and enzymes (e.g., proteases). Strains producing high levels of omega-6 fatty acids have also been isolated. Such strains are useful for producing omega-6 fatty acids which, in turn, are useful starting materials for chemical synthesis of prostaglandins and other eicosanoids. Strains producing more than 25% of total fatty acids as omega-6 fatty acids have been isolated by the method described herein.

The harvested biomass can be dried (e.g., spray drying, tunnel drying, vacuum drying, or a similar process) and used as a feed or food supplement for any animal whose meat or products are consumed by humans. Similarly, extracted omega-3 HUFAs can be used as a feed or food supplement. Alternatively, the harvested and washed biomass can be used directly (without drying) as a feed supplement. To extend its shelf life, the wet biomass can be acidified (approximate pH=3.5–4.5) and/or pasteurized or flash heated to inactivate enzymes and then canned, bottled or packaged under a vacuum or non-oxidizing atmosphere (e.g., $N_2$ or $CO_2$). The term "animal" means any organism belonging to the kingdom Animalia. The term "animal" means any organism belonging to the kingdom Animalia and includes, without limitation, any animal from which poultry meat, seafood, beef, pork or lamb is derived. Seafood is derived from, without limitation, fish, shrimp and shellfish. The term "products" includes any product other than meat derived from such animals, including, without limitation, eggs or other products. When fed to such animals, omega-3 HUFAs in the harvested biomass or extracted omega-3 HUFAs are incorporated into the flesh, eggs or other products of such animals to increase the omega-3 HUFA content thereof.

It should be noted that different animals have varying requirements to achieve a desired omega-3 HUFA content. For example, ruminants require some encapsulation technique for omega-3 HUFAs to protect these Unsaturated fatty acids from breakdown or saturation by the rumen microflora prior to digestion and absorption of the omega-3 HUFAs by the animal. The omega-3 HUFA's can be "protected" by coating the oils or cells with a protein (e.g., zeain) or other substances which cannot be digested (or are poorly digested) in the rumen. This allows the fatty acids to pass undamaged through the ruminant's first stomach. The protein or other "protectant" substance is dissolved in a solvent prior to coating the cells or oil. The cells can be pelleted prior to coating with the protectant. Animals having high feed conversion ratios (e.g., 4:1–6:1) will require higher concentrations of omega-3 HUFAs to achieve an equivalent incorporation of omega-3 HUFAs as animal with low feed conversion ratios (2:1–3:1). Feeding techniques can be further optimized with respect to the period of an animal's life that harvested biomass or extracted omega-3 HUFAs must be fed to achieve a desired result.

For most feed applications, the oil content of the harvested cells will be approximately 25–50% afdw, the remaining material being protein and carbohydrate. The protein can contribute significantly to the nutritional value of the cells as several of the strains that have been evaluated have all of the essential amino acids and would be considered a nutritionally balanced protein.

In a preferred process, the freshly harvested and washed cells (harvested by belt filtration, rotary drum filtration, centrifugation, etc.) containing omega-3 HUFAs can be mixed with any dry ground grain in order to lower the water content of the harvested cell paste to below 40%. moisture. For example, corn can be used and such mixing will allow the cell paste/corn mixture to be directly extruded, using common extrusion procedures. The extrusion temperatures and pressures can be modified to vary the degree of cell rupture in the extruded product (from all whole cells to 100% broken cells). Extrusion of the cells in this manner does not appear to greatly reduce the omega-3 HUFA content of the cells, as some of the antioxidants in the grain may help protect the fatty acids from oxidation, and the extruded matrix may also help prevent oxygen from readily reaching the fatty acids. Synthetic or natural antioxidants can also be added to the cell paste/grain mixture prior to extrusion. By directly extruding the cell paste/grain mixture, drying times and costs can be greatly reduced, and it allows manipulation of the bioavailability of the omega-3 HUFAs for feed supplement applications by degree of cell rupture. The desired degree of cell rupture will depend on various factors, including the acceptable level of oxidation (increased cell rupture increases likelihood of oxidation) and the required degree of bioavailability by the animal consuming the extruded material.

The unicellular fungal strains isolated by the method described readily flocculate and settle, and this process can be enhanced by adjusting the pH of the culture to pH≦7.0. A 6-fold concentration of the cells within 1–2 minutes can be facilitated by this process. The method can therefore be employed to preconcentrate the cells prior to harvesting, or to concentrate the cells to a very high density prior to nitrogen limitation. Nitrogen limitation (to induce higher lipid production) can therefore be carried out in a much smaller reactor, or the cells from several reactors consolidated into one reactor.

A variety of procedures can be employed in the recovery of the microbial cells from the culture medium. In a preferred recovery process, the cells produced by the subject process are recovered from the culture medium by separation by conventional means, such as by filtration or centrifugation. The cells can then be washed; frozen, lyophilized, or spray dried; and stored under a non-oxidizing atmosphere of a gas such as $CO_2$ or $N_2$ (to eliminate the presence of $O_2$), prior to incorporation into a processed food or feed product.

Cellular lipids containing the omega-3 highly unsaturated fatty acids can also be extracted from the microbial cells by any suitable means, such as by supercritical fluid extraction, or by extraction with solvents such as chloroform, hexane, methylene chloride, methanol, and the like, and the extract evaporated under reduced pressure to produce a sample of concentrated lipid material. The omega-3 highly unsaturated fatty acids in this preparation may be further concentrated by hydrolyzing the lipids and concentrating the highly unsaturated fraction by employing traditional methods such as urea adduction or fractional distillation (Schlenk, 1954), column chromatography (Kates, 1986), or by supercritical fluid fractionation (Hunter, 1987). The cells can also be broken or lysed and the lipids extracted into vegetable or other edible oil (Borowitzka and Borowitzka, 1988). The extracted oils can be refined by well-known processes routinely employed to refine vegetables oils (e.g. chemical refining or physical refining). These refining processes remove impurities from extracted oils before they are used or sold as edible oils. The refining process consists of a series of processes to degum, bleach, filter, deodorize and polish the extracted oils. After refining, the oils can be used directly as a feed or food additive to produce omega-3

HUFA enriched products. Alternatively, the oil can be further processed and purified as outlined below and then used in the above applications and also in pharmaceutical applications.

In a preferred process, a mixture of high purity omega-3 HUFAs or high purity HUFAs can be easily concentrated from the extracted oils. The harvested cells (fresh or dried) can be ruptured or permeabilized by well-known techniques such as sonication, liquid-shear disruption methods (e.g., French press of Manton-Gaulin homogenizer), bead milling, pressing under high pressure, freeze-thawing, freeze pressing, or enzymatic digestion of the cell wall. The lipids from the ruptured cells are extracted by use of a solvent or mixture of solvents such as hexane, chloroform, ether, or methanol. The solvent is removed (for example by a vacuum rotary evaporator, which allows the solvent to be recovered and reused) and the lipids hydrolyzed by using any of the well-known methods for converting triglycerides to free fatty acids or esters of fatty acids including base hydrolysis, acid hydrolysis, or enzymatic hydrolysis. The hydrolysis should be carried out at as low a temperature as possible (e.g., room temperature to 60° C.) and under nitrogen to minimize breakdown of the omega-3 HUFAs. After hydrolysis is completed, the nonsaponifiable compounds are extracted into a solvent such as ether, hexane or chloroform and removed. The remaining solution is then acidified by addition of an acid such as HCl, and the free fatty acids extracted into a solvent such as hexane, ether, or chloroform. The solvent solution containing the free fatty acids can then be cooled to a temperature low enough for the non-HUFAs to crystallize, but not so low that HUFAs crystallize. Typically, the solution is cooled to between about –60° C. and about –74° C. The crystallized fatty acids (saturated fatty acids, and mono-, di-, and tri-enoic fatty acids) can then be removed (while keeping the solution cooled) by filtration, centrifugation or settling. The HUFAs remain dissolved in the filtrate (or supernatant). The solvent in the filtrate (or supernatant) can then be removed leaving a mixture of fatty acids which are >90% purity in either omega-3 HUFAs or HUFAs which are greater than or equal to 20 carbons in length. The purified omega-3 highly unsaturated fatty acids can then be used as a nutritional supplement for humans, as a food additive, or for pharmaceutical applications. For these uses the purified fatty acids can be encapsulated or used directly. Antioxidants can be added to the fatty acids to improve their stability.

The advantage of this process is that it is not necessary to go through the urea complex process or other expensive extraction methods, such as supercritical $CO_2$ extraction or high performance liquid chromatography, to remove saturated and mono-unsaturated fatty acids prior to cold crystallization. This advantage is enabled by starting the purification process with an oil consisting of a simple fatty acid profile such as that produced by Thraustochytrids (3 or 4 saturated or monounsaturated fatty acids with 3 or 4 HUFAs, two groups of fatty acids widely separated in terms of their crystallization temperatures) rather than a complex oil such as fish oil with up to 20 fatty acids (representing a continuous range of saturated, mono-, di-, tri-, and polyenoic fatty acids, and as such, a series of overlapping crystallization temperatures).

In a preferred process, the omega-3 HUFA enriched oils can be produced through cultivation of strains of the genus Thraustochytrium. After the oils are extracted from the cells by any of several well-known methods, the remaining extracted (lipids removed) biomass which is comprised mainly of proteins and carbohydrates, can be sterilized and returned to the fermenter, where the strains of Thraustochytrium can directly recycle it as a nutrient source (source of carbon and nitrogen). No prehydrolysis or predigestion of the cellular biomass is necessary. Extracted biomass of the genus Schizochytrium can be recycled in a similar manner if it is first digested by an acid and/or enzymatic treatment.

As discussed in detail above, the whole-cell biomass can be used directly as a food additive to enhance the omega-3 highly unsaturated fatty acid content and nutritional value of processed foods for human intake or for animal feed. When used as animal feed, omega-3 HUFAs are incorporated into the flesh or other products of animals. The complex lipids containing these fatty acids can also be extracted from the whole-cell product with solvents and utilized in a more concentrated form (e.g., encapsulated) for pharmaceutical or nutritional purposes and industrial applications. A further aspect of the present invention includes introducing omega-3 HUFAs from the foreoging sources into humans for the treatment of various diseases. As defined herein, "treat" means both the remedial and preventative practice of medicine. The dietary value of omega-3 HUFAs is widely recognized in the literature, and intake of omega-3 HUFAs produced in accordance with the present invention by humans is effective for treating cardiovascular diseases, inflammatory and/or immunological diseases and cancer.

The present invention will be described in more detail by way of working examples. Species meeting the selection criteria described above have not been described in the prior art. By employing these selection criteria, the inventor isolated over 25 potentially promising strains from approximately 1000 samples screened. Out of the approximate 20,500 strains in the American Type Culture Collection (ATCC), 10 strains were later identified as belonging to the same taxonomic group as the strains isolated by the inventor. Those strains still viable in the Collection were procured and used to compare with strains isolated and cultured by the disclosed procedures. The results of this comparison are presented in Examples 5 and 6 below.

Since the filing of the parent case, recent developments have resulted in revision of the taxonomy of the Thraustochytrids. The most recent taxonomic theorists place them with the algae. However, because of the continued taxonomic uncertainty, it would be best for the purposes of the present invention to consider the strains as Thraustochydrids (Order: Thraustochytriales; Family: Thraustochytriaceae; Genus: Thraustochytrium or Schizochytrium). The most recent taxonomic changes are summarized below.

All of the strains of unicellular microorganisms disclosed and claimed herein are members of the order Thraustochytriales. Thraustochytrids are marine eukaryotes with a rocky taxonomic history. Problems with the taxonomic placement of the Thraustochytrids have been reviewed most recent by Moss (1986), Bahnweb and Jackle (1986) and Chamberlain and Moss (1988). For convenience purposes, the Thraustochytrids were first placed by taxonomists with other colorless zoosporic eukaryotes in the Phycomycetes (algae-like fungi). The name Phycomycetes, however, was eventually dropped from taxonomic status, and the Thraustochytrids retained in the Oomycetes (the biflagellate zoosporic fungi). It was initially assumed that the Oomycetes were related to the heterokont algae, and eventually a wide range of ultrastructural and biochemical studies, summarized by Barr (1983) supported this assumption. The Oomycetes were in fact accepted by Leedale (1974) and other phycologists as part of the heterokont algae. However, as a matter of convenience resulting from their heterotrophic nature, the Oomycetes and Thraustochytrids have been largely studied by mycologists (scientists who study fungi) rather than phycologists (scientists who study algae).

From another taxonomic perspective, evolutionary biologists have developed two general schools of thought as to how eukaryotes evolved. One theory proposes an exogenous origin of membrane-bound organelles through a series of endosymbioses (Margulis (1970); e.g., mitochondria were derived from bacterial endosymbionts, chloroplasts from cyanophytes, and flagella from spirochaetes). The other theory suggests a gradual evolution of the membrane-bound organelles from the non-membrane-bounded systems of the prokaryote ancestor via an autogenous process (Cavalier-Smith 1975). Both groups of evolutionary biologists however, have removed the Oomycetes and thraustochytrids from the fungi and place them either with the chromophyte algae in the kingdom Chromophyta (Cavalier-Smith 1981) or with all algae in the kingdom protoctista (Margulis and Sagan (1985).

With the development of electron microscopy, studies on the ultrastructure of the zoospores of two genera of Thraustochytrids, Thraustochytrium and Schizochytrium, (Perkins 1976; Kazama 1980; Barr 1981) have provided good evidence that the Thraustochytriaceae are only distantly related to the Oomycetes. Additionally, more recent genetic data representing a correspondence analysis (a form of multivariate statistics) of 5 S ribosomal RNA sequences indicate that Thraustochytriales are clearly a unique group of eukaryotes, completely separate from the fungi, and most closely related to the red and brown algae, and to members of the Oomycetes (Mannella et al. 1987). Recently however, most taxonomists have agreed to remove the Thraustochytrids from the Oomycetes (Bartnicki-Garcia 1988).

In summary, employing the taxonomic system of Cavalier-Smith (1981, 1983), the Thraustochytrids are classified with the chromophyte algae in the kingdom Chromophyta, one of the four plant kingdoms. This places them in a completely different kingdom from the fungi, which are all placed in the kingdom Eufungi. The taxonomic placement of the Thraustochytrids is therefore summarized below:

Kingdom: Chromophyta
Phylum: Heterokonta
Order: Thraustochytriales
Family: Thraustochytriaceae
Genus: Thraustochytrium or Schizochytrium Despite the Uncertainty of taxonomic placement within higher classifications of Phylum and Kingdom, the Thraustochytrids remain a distinctive and characteristic grouping whose members remain classifiable within the order Thraustochytriales.

Omega-3 highly unsaturated fatty acids are nutritionally important fatty acids for both humans and animals. Currently the only commercially available source of these fatty acids is from fish oil. However, there are several significant problems with the use of fish oil as a food or feed additive or supplement. First and most significantly, fish oils have a strong fishy taste and odor, and as such cannot be added to processed foods as a food additive, without negatively affecting the taste of the food product. This is also true for many of its applications as an animal food or feed additive. For example, experiments by the inventor and others have indicated that laying hens readily go off their feed when fed for more than a few days on feed enriched with fish oils. Fish oils are very unstable, easily becoming rancid and thereby decreasing the palatability and nutritional value of feed.

Secondly, fish oils generally only contain 20–30% omega-3 HUFAs. Desirable omega-3 HUFA contents in marine larval fish and shrimp feeds can be as high as 5–10% of their dry weight. To constitute an appropriate synthetic diet containing 5–10% omega-3 HUFAs could require a diet of 15–30% fish oil. Such a synthetic diet would not be the most suitable for these larval organisms either in terms of palatability, digestibility, or stability (Sargent et al. (1989). In terms of human nutrition, the other 70–80% of fatty acids in fish oil are saturated and omega-6 fatty acids, fatty acids which can have deleterious health effects for humans. Processes for the isolation of pure omega-3 fatty acids from fish oils are involved and expensive, resulting in very high prices ($200–$1000/g) for pure forms of these fatty acids, much too expensive for use as a food or feed additive (Sigma Chemical, Co., 1988; CalBiochem Co., 1988).

Third, most feeds currently used by the aquaculture industry are grain based feeds, and as such, are relatively low in omega-3 HUFA content. Recent surveys of seafood products have demonstrated that fish and shrimp produced by aquaculture farms generally only have ⅓–½ the omega-3 HUFA content of wild caught fish and shrimp (Pigott 1989). For aquacultured organisms, many which are prized because of their mild, non-fishy taste, increasing the fish oil content of their food is not effective, because it results in a fish-tasting product.

As a result of the problems described above, there is an important need for development of alternative (non-fish based) sources of omega-3 HUFAs.

The microbial product of the present invention can be used as a food or feed supplement to provide an improved source of omega-3 highly unsaturated fatty acids which has significant advantages over conventional sources. Poultry fed a diet supplemented with the microbial product incorporate the omega-3 highly unsaturated fatty acids into body tissues and into eggs. The eggs exhibit no fishy odor or taste, no change in yolk color. The poultry do not stop eating the supplemented feed, as they do with fish oil-supplemented feed. Feed supplemented with the microbial product of the present invention has a normal shelf life and does not become rancid upon standing at room temperature for several days. The eggs and flesh of poultry fed according to the invention are useful in human nutrition as sources of omega-3 highly unsaturated fatty acids, yet are low in omega-6 fatty acid content and lack a fishy flavor.

The microbial product of the present invention is also of value as a source of omega-3 highly unsaturated fatty acids for fish, shrimp and other products produced by aquaculture. The product can be added directly as a supplement to the feed or it can be fed to brine shrimp or other live feed organisms intended for consumption by the aquacultured product. The use of such supplement enables the fish or shrimp farmer to bring to market an improved product retaining the taste advantages provided by aquaculture but having the high omega-3 highly unsaturated fatty acid content of wild caught fish coupled to the additional health advantage of reduced omega-6 fatty acid content.

EXAMPLES

Example 1

Collection and Screening

Figure 1:
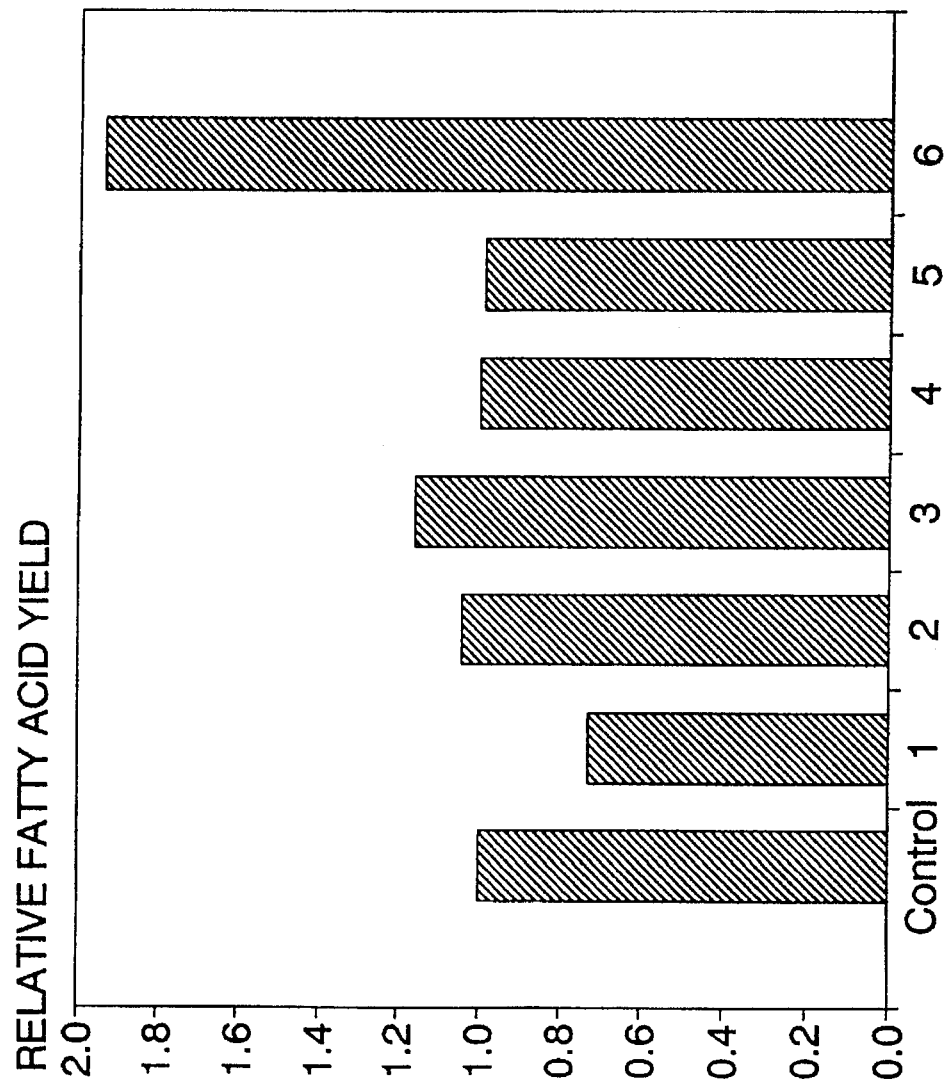
FIG. 1 is a bar graph showing the effects of various media supplements on fatty acid yield, using Thraustochytrium sp. UT42-2 (ATCC No. 20891), a strain isolated according to the selection method of the invention as a test strain. The experimental procedure is described in Example 2. Ordinate: fatty acid yield, normalized to control, FFM media without supplements. Abscissa: specific additions, 1) 2x "B"-vitamin mix; 2) 2x "A" vitamin mix; 3) 2x PI metals; 4) 28 mg/l $KH_2PO_4$; 5) treatments 2), 3) and 4) combined; and 6) 480 mg/l $KH_2PO_4$.

A 150 ml water sample was collected from a shallow, inland saline pond and stored in a sterile polyethylene bottle. Special effort was made to include some of the living plant material and naturally occurring detritus (decaying plant and animal matter) along with the water sample. The sample was placed on ice until return to the laboratory. In the lab, the water sample was shaken for 15–30 seconds, and 1–10 ml of the sample was pipetted or poured into a filter unit containing 2 types of filters: 1) on top, a sterile 47 mm diameter Whatman #4 filter having a pore size about 25 µm; and 2) underneath the Whatman filter, a 47 mm diameter polycarbonate filter with about 1.0 µm pore size. Given slight variations of nominal pore sizes for the filters, the cells collected on the polycarbonate filter range in size from about 1.0 µm to about 25 µm.

The Whatman filter was removed and discarded. The polycarbonate filter was placed On solid F-1 media in a petri plate, said media consisting of (per liter): 600 ml seawater (artificial seawater can be used), 400 ml distilled water, 10 g agar, 1 g glucose, 1 g protein hydrolysate, 0.2 g yeast extract, 2 ml 0.1M $KH_2PO_4$, 1 ml of a vitamin solution (A-vits) (Containing 100 mg/l thiamine, 0.5 mg/l biotin, and 0.5 mg/l cyanocobalamin), 5 ml of a trace metal mixture (PII metals, containing per liter: 6.0 g $Na_2EDTA$, 0.29 g $FeCl_3 6H_2O$, 6.84 g $H_3BO_3$, 0.86 $MnCl_2 4H_2O$, 0.06 g $ZnCl_2$, 0.026 g $CoCl_2 6H_2O$, (0.052 g $NiSO_4 H_2O$, 0.002 g $CuSo_4 5H_2O$, and 0.005 g $Na_2MoO_4 2H_2O$, and 500 mg each of streptomycin sulfate and penicillin-G. The agar plate was incubated in the dark at 30° C. After 2–4 days numerous colonies appeared on the filter. Colonies of unicellular fungi (except yeast) were picked from the plate and restreaked on a new plate of similar media composition. Special attention was made to pick all colonies consisting of colorless of white cells. The new plate was incubated at 30° C. and single colonies picked after a 2–4 day incubation period. Single colonies were then picked and placed in 50 ml of liquid medium containing the same organic enrichments as in the agar plates. These cultures were incubated for 2–4 days at 30° C. on a rotary shaker table (100–200 rpm). When the cultures appeared to reach maximal density, 20–40 ml of the culture was harvested, centrifuged and lyophilized. The sample was then analyzed by standard, well-known gas chromatographic techniques (e.g., Lepage and Roy, 1984) to identify the fatty acid content of the strain. Those strains with omega-3 highly unsaturated fatty acids were thereby identified, and cultures of these strains were maintained for further screening.

Using the collection and screening process outlined above, over 150 strains of unicellular fungi have been isolated which have omega-3 highly unsaturated fatty acid contents up to 32% total cellular ash-free dry weight, and which exhibit growth over a temperature range from 15°–48° C. Strains can also be isolated which have less than 1% (as % of total fatty acids) of the undesirable C20:4w6 and C22:5w6 highly unsaturated fatty acids. Strains of these fungi can be repeatedly isolated from the same location using the procedure outlined above. A few of the newly isolated strains have very similar fatty acid profiles. The possibility that some are duplicate isolates of the same strain cannot be ruled out at present. Further screening for other desirable traits such as salinity tolerance or ability to use a variety of carbon and nitrogen sources can then be carried out using a similar process.

Example 2

Maintaining unrestricted cell growth: phosphorus

Cells of Thraustochytrium sp. U42-2 (ATCC No. 20891), a strain isolated by the method in Example 1, were picked from solid F-medium and inoculated into 50 ml of modified FFM medium (Fuller et al., 1964). This medium containing: seawater, 1000 ml; glucose, 1.0 g; gelatin hydrolysate, 1.0 g; liver extract, 0.01 g; yeast extract, 0.1 g; PII metals, 5 ml; 1 ml B-vitamins solution (Goldstein et al., 1969); and 1 ml of an antibiotic solution (25 g/l streptomycin sulfate and penicillin-G). 1.0 ml of the vitamin mix (pH 7.2) contains: thiamine HCl, 200 µg; biotin, 0.5 µg; cyanocobalamin, 0.05 µg; nicotinic acid, 100 µg; calcium pantothenate, 100 µg; riboflavin, 5.0 µg; pyridoxine HCl, 40.0 µg; pyridoxamine 2 HCl, 20.0 µg; p-aminobenzoic acid, 10 µg; chlorine HCl, 500 µg; inositol, 1.0 mg; thymine, 0.8 mg; orotic acid, 0.26 mg; folinic acid, 0.2 µg; and folic acid, 2.5 µg. 250 ml erlenmeyer flasks with 50 ml of this medium were placed on an orbital shaker (200 rpm) at 27° C. for 2–4 days, at which time the culture had reached their highest densities. One ml of this culture was transferred to a new flask of modified FFM medium, with the extra addition of one of the following treatments on a per liter basis: 1) 1 ml of the B-vitamin mix; 2) 1 ml of A-vitamin solution; 3) 5 ml PII Metals; 4) 2 ml of 0.1M $KH_2PO_2$ (≈28 mg); 5) treatments 2, 3, and 4 combined; and 6) 480 mg $KH_2PO_4$. One ml of the culture was also transferred to a flask of modified FFM medium which had no extra additions made to it and served as a control for the experiment. The cultures were incubated for 48 hr. at 27° C. on a rotary shaker (200 rpm). The cells were then harvested by centrifugation and the fatty acids were quantified by gas chromatography. The results are illustrated in FIG. 1 and Table 1. In FIG. 1, the yields are plotted as ratios of the control, whose relative yield is therefore 1.0. Treatments 1–6 are as follows: 1) 2x concentration of B vitamins; 2) 2x concentration of A vitamins; 3) 2x concentration of trace metals; 4) 2x concentration of (B vitamins+ phosphate+trace metals); 5) 2x concentration of phosphate; and 6) 24 mg phosphate per 50 ml (0.48 g per liter). Only the treatment of adding 0.48 g $KH_2PO_4$ per liter resulted in enhanced growth and resulted in significantly increased fatty acid yield.

TABLE 1

Effect of various nutrient additions on the yield of fatty acids in *Thraustochytrium sp.* U42-2 (ATCC No. 20891)

| Treatment | Fatty Acid Yield mg/liter |
| --- | --- |
| Control | 23 |
| 2 × concentration of B vitamin mix | 17 |
| 2 × concentration of A vitamin mix | 24 |
| 2 × concentration trace metals | 27 |
| 2 × concentration B vitamin mix, 2 × $PO_4$ and 2 × concentration trace metals | 24 |
| 2 × concentration $PO_4$ | 23 |
| 24 mg phosphate per 50 ml | 45 |

Example 3

Maintaining unrestricted growth: $PO_4$ and yeast extract

Cells of *Schizochytrium aggregatum* (ATCC 28209) were picked from solid F-1 medium and inoculated into 50 ml of FFM medium. The culture was placed on a rotary shaker (200 rpm) at 27° C. After 3–4 days, 1 ml of this culture was transferred to 50 ml of each of the following treatments: 1) FFM medium (as control); and 2) FFM medium with the addition of 250 mg/l $KH_2PO_4$ and 250 mg/l yeast extract. These cultures were placed on a rotary shaker (200 rpm) at 27° C. for 48 hr. The cells were harvested and the yield of cells quantified. In treatment 1, the final concentration of cells on an ash-free dry weight basis was 616 mg/l. In treatment 2, the final concentration of cells was 1675 mg/l, demonstrating the enhanced effect of increasing $PO_4$ and yeast extract concentrations in the culture medium.

Example 4

Maintaining unrestricted growth: substitution of corn steep liquor for yeast extract Cells of *Schizochytrium sp.* S31 (ATCC No. 20888) were picked from solid F-1 medium and placed into 50 ml of M-5 medium. This medium consists of (on a per liter basis): NaCl, 25 g; $MgSO_4.7H_2O$, 5 g; KCl, 1 g; $CaCl_2$, 200 mg; glucose, 5 g; glutamate, 5 g; $KH_2PO_4$, 1 g; PII metals, 5 ml; A-vitamins solution, 1 ml; and antibiotic solution, 1 ml. The pH of the solution was adjusted to 7.0 and the solution was filter sterilized. Sterile solutions of corn steep liquor (4 g/40 ml; pH 7.0) and yeast extract 1 g/40 ml; pH 7.0) were prepared. To one set of M-5 medium flasks, the following amount of yeast extract solution was added: 1) 2 ml; 2) 1.5 ml; 3) 1 ml; 4) 0.5 ml; and 5) 0.25 ml. To another set of M-5 medium flasks the yeast extract and corn steep liquor solutions were added at the following levels: 1) 2 ml yeast extract; 2) 1.5 ml yeast extract and 0.5 ml corn steep liquor; 3) 1.0 ml yeast extract and 1.0 ml corn steep liquor; 4) 0.5 ml yeast extract and 1.5 ml corn steep liquor; and 5) 2 ml corn steep liquor. One ml of the culture in F-1 medium was used to inoculate each flask. They were placed on a rotary shaker at 27° C. for 48 hr. The cells were harvested by centrifugation and the yield of cells (as ash-free dry weight) was determined. The results are shown in Table 2. The results indicate the addition of yeast extract up to 0.8 g/l of medium can increase the yield of cells. However, addition of corn steep liquor is even more effective and results in twice the yield of treatments with added yeast extract. This is very advantageous for the economic production of cells as corn steep liquor is much less expensive than yeast extract.

TABLE 2

| Treatment (Amount Nutrient Supplement Added) | Ash-Free Dry Weight (mg/l) |
| --- | --- |
| 2.0 ml yeast ext. | 4000 |
| 1.5 ml yeast ext. | 4420 |
| 1.0 ml yeast ext. | 4300 |
| 0.5 ml yeast ext. | 2780 |
| 0.25 ml yeast ext. | 2700 |
| 2.0 ml yeast ext. | 4420 |
| 1.5 ml yeast ext. + 0.5 ml CSL* | 6560 |
| 1.0 ml yeast ext. + 1.0 ml CSL | 6640 |
| 0.5 ml yeast ext. + 1.5 ml CSL | 7200 |
| 2.0 ml CSL | 7590 |

*CSL = corn steep liquor

Example 5

Enhanced highly unsaturated fatty acid content of strains isolated by method in Example 1 compared to ATCC strains (previously known strains)

A battery of 151 newly isolated strains, selected according to the method described in Example 1, were sampled in late exponential phase growth and quantitatively analyzed for highly unsaturated fatty acid content by gas-liquid chromatography. All strains were grown either in M1 medium or liquid FFM medium, whichever gave highest yield of cells. Additionally, five previously isolated Thraustochytrium or Schizochytrium species were obtained from the American Type Culture Collection, representing all the strains which could be obtained in viable form from the collection. These strains were: *T. aureum* (ATCC No. 28211), *T. aureum* (ATCC No. 34304), *T. roseum* (ATCC No. 28210), *T. straitum* (ATCC No. 34473) and *S. aggregatum* (ATCC No. 28209). The strains all exhibited abbreviated growth in conventional media, and generally showed improved growth in media of the present invention, including M5 medium and FFM medium, Example 2. The fatty acids production of each of the known strains was measured as described, based upon the improved growth of the strains in media of the invention.

Fatty acid peaks were identified by the use of pure compounds of known structure. Quantitation, in terms of percent by weight of total fatty acids, was carried out by integrating the chromatographic peaks. Compounds identified were: palmitic acid (C16:0), C20:4w6 and C22:1 (which were not resolved separately by the system employed), C20:5w3, C22:5w6, C22:5w3, and C22:6w3. The remainder, usually lower molecular weight fatty acids, were included in the combined category of "other fatty acids." Total omega-3 fatty acids were calculated as the sum of 20:5w3, 22:5w3 and 22:6w3. Total omega-6 fatty acids were calculated as the sum of the 20:4/22:1 peak and the 22:5w6 peak.

Figure 2:
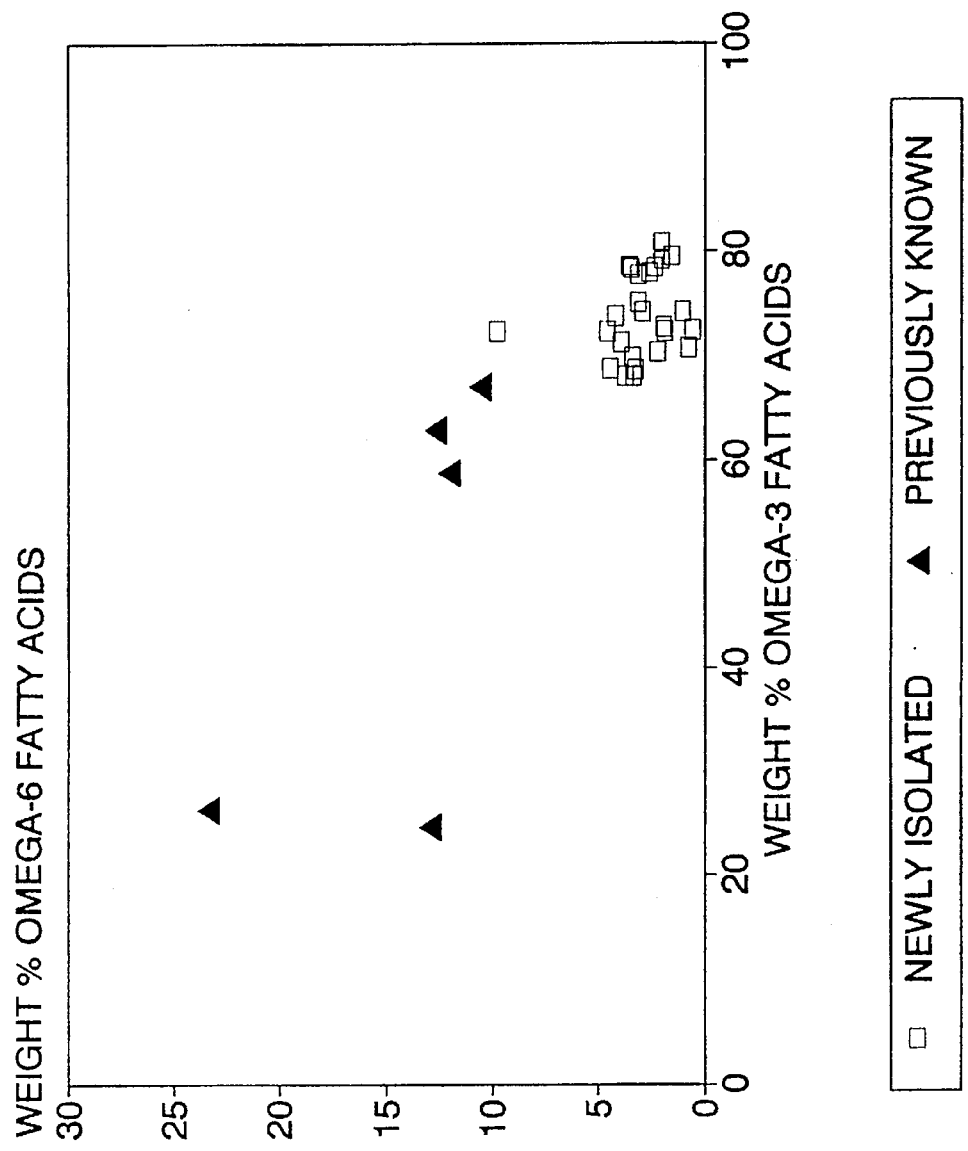
FIG. 2 is a graphical representation of highly unsaturated fatty acid production in newly isolated strains of the invention, represented by ■, and previously isolated strains represented by +. Each point represents a strain, the position of each point is determined by the percent by weight of total fatty acids which were omega-3 highly unsaturated fatty acids (abscissa) and the percent by weight of total fatty acids which were omega-6 fatty acids (ordinate). Only those strains of the invention were plotted wherein less than 10.6% (w/w) of total fatty acids were omega-6 and more than 67% of total fatty acids were omega-3. Data from Table 4.
Figure 3:
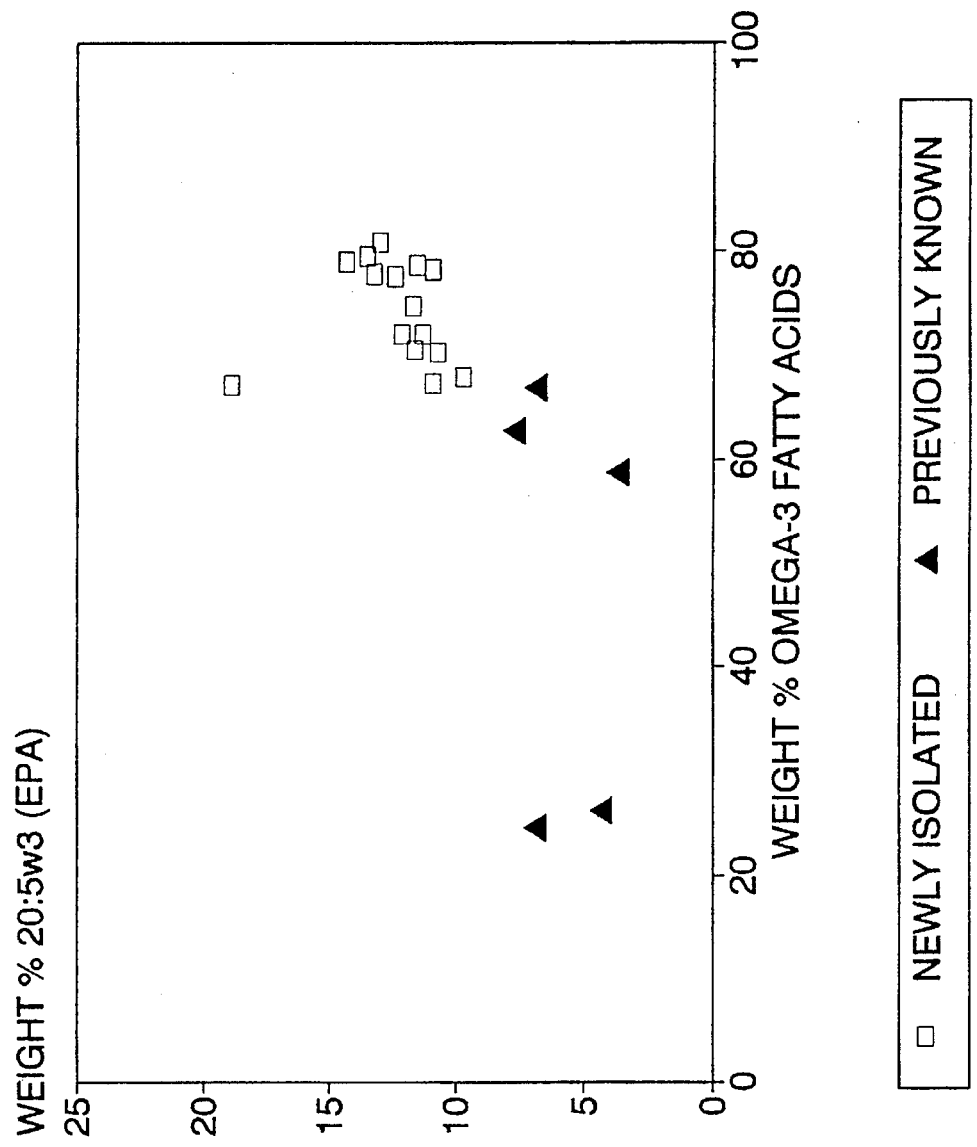
FIG. 3 is a graphical representation of highly unsaturated fatty acid production in newly isolated strains of the invention, represented by ■, and previously isolated strains, represented by +. Each point represents a strain, the position of each point is determined by the percent by weight of total fatty acids which were omega-3 highly unsaturated fatty acids (abscissa) and percent of weight of total fatty acids which were eicosapentaenoic acid (EPA C20:5w3) (ordinate). Only those strains of the invention were plotted wherein more than 67% (w/w) of total fatty acids were omega-3 and more than 7.8% (w/w) of total fatty acids were C20:5w3.
Figure 4:
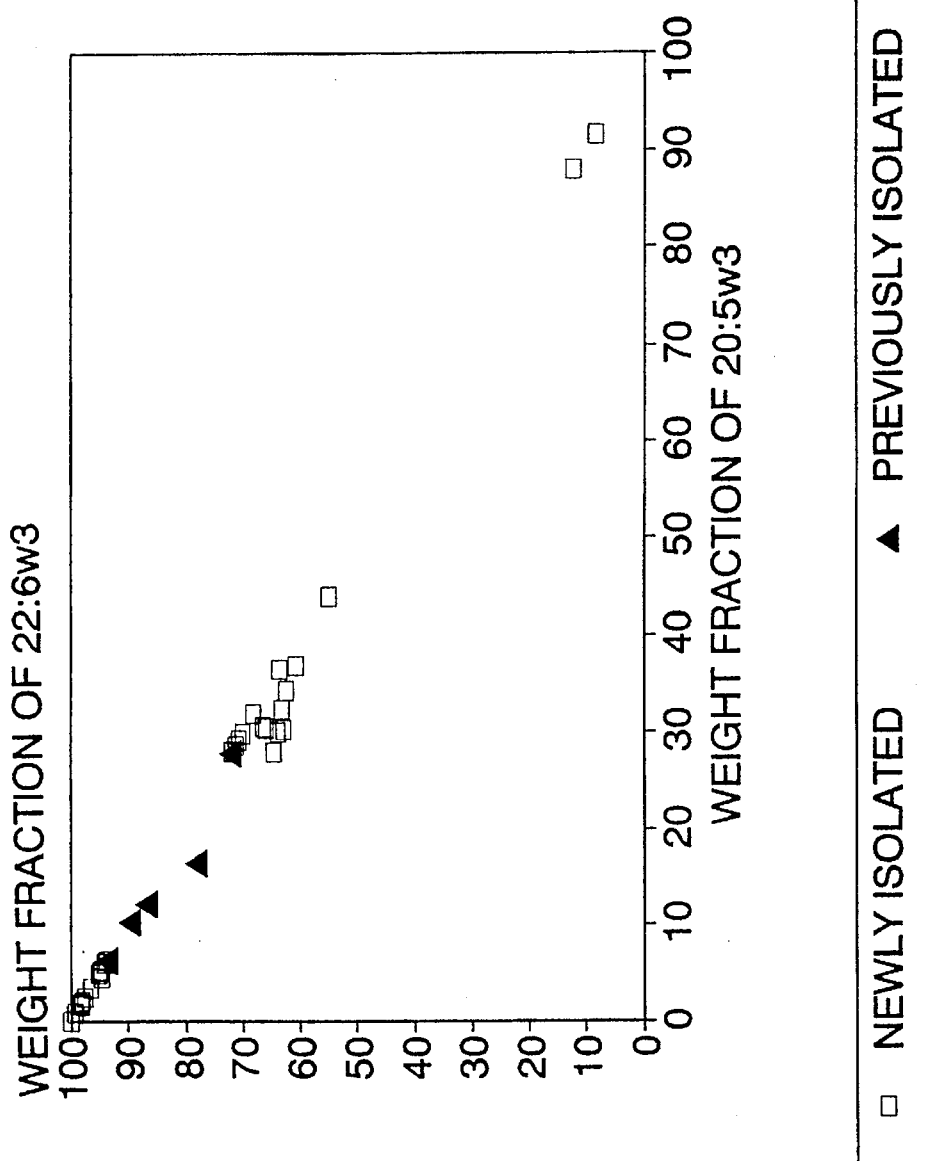
FIG. 4 is a graphical representation of omega-3 highly unsaturated fatty acid composition in newly isolated strains of the invention, represented by □, and previously isolated strains, represented by +. Each point represents a separate strain. Values on the abscissa are weight fraction of total omega-3 highly unsaturated fatty acids which were C20:5w3 and on the ordinate are weight fraction of total omega-3 fatty highly unsaturated acids which were C22:6w3. Only strains of the invention were plotted having either a weight fraction of C20:5w3 28% or greater, or a weight fraction of C22:6w3 greater than 93.6%.

The results are shown in Tables 3–4 and illustrated in FIGS. 2–4. From Table 3 it can be seen that large numbers of strains can be isolated by the method of the invention, and that large numbers of strains outperform the previously known strains by several important criteria. For example, 102 strains produced at least 7.8% by weight of total fatty acids C20:5w3, a higher percentage of that fatty acid than any previously known strain. Strains 23B (ATCC No. 20892) and 12B (ATCC No. 20890) are examples of such strains. Thirty (30) strains of the invention produced at least 68% by weight of total fatty acids as omega-3 fatty acids, more than any previously known strain. Strain 23B (ATCC No. 20892) is an example of such strains. Seventy-six (76) strains of the invention yielded not more than 10% by weight of total fatty acids as omega-6 fatty acids, considered undesirable components of the human diet, lower than any previously known strain. Strains 23B (ATCC No. 20892) and 12B (ATCC No. 20890.) are examples of such strains. In addition, there are 35 strains of the invention that produce more than 25% by weight of total fatty acids as omega-6 fatty acids, more than any previously known strain. While such strains may not be useful for dietary purposes, they are useful as feedstock for chemical synthesis of eicosanoids starting from omega-6 fatty acids.

In addition, the data reveal many strains of the invention which produce a high proportion of total omega-3 fatty acids as C22:6w3. In Table 4, 48 of the strains shown in Table 2 were compared to the previously known strains, showing each of C20:5w3, C22:5w3 and C22:6w3 as percent by weight of total omega-3 content. Fifteen strains had at least 94% by weight of total omega-3 fatty acids as C22:6w3, more than any previously known strain. Strain S8 (ATCC No. 20889) was an example of such strains. Eighteen strains had at least 28% by weight of total omega-3 fatty acids as C20:5w3, more than any previously known strain. Strain 12B (ATCC No. 20890) was an example of such strains.

FIG. 2 illustrates the set of strains, isolated by the method in Example 1, that have more than 67% omega-3 fatty acids (as % of total fatty acids) and less than 10.6% omega-6 fatty acids (as % of total fatty acids). All of the previously known strains had less than 67% omega-3 fatty acids (as % of total fatty acids) and greater than 10.6% omega-6 (as % of total fatty acids).

FIG. 3 illustrates the set of strains, isolated by the method in Example 1, that have more than 67% omega-3 fatty acids (as % of total fatty acids) and greater than 7.5% C20:5w3 (as % of total fatty acids). All of the previously known strains had less than 67% omega-3 fatty acids (as % of total fatty acids) and less than 7.8% C20:5w3 (as % of total fatty acids).

TABLE 3

LIST OF STRAINS AND COMPOSITIONS UNDER STANDARD SCREENING CONDITIONS

| PERCENT OF TOTAL FATTY ACIDS | | | | | | | Total | Total | |
| --- | --- | --- | --- | --- | --- | --- | --- | --- | --- |
| C16:0 | C20:4w6 | C20:5w3 | C22:5w6 | C22:5w3 | C22:6w3 | Other FA | Omega3 | Omega6 | Strain |
| 30.4% | 2.8% | 6.6% | 3.2% | 0.2% | 8.3% | 48.5% | 15.1% | 6.0% | 21 |
| 22.9% | 0.4% | 2.3% | 15.5% | 0.5% | 47.0% | 11.5% | 49.7% | 15.9% | ATCC20889 |
| 14.9% | 6.5% | 12.0% | 11.8% | 0.4% | 49.7% | 4.7% | 62.1% | 18.3% | U40-2 |
| 40.3% | 1.7% | 3.8% | 8.6% | 0.0% | 8.2% | 37.4% | 12.0% | 10.2% | 21B |
| 20.7% | 0.4% | 7.8% | 0.0% | 0.0% | 1.1% | 70.1% | 8.9% | 0.4% | BG1 |
| 26.0% | 5.7% | 1.5% | 9.7% | 0.7% | 9.7% | 46.7% | 11.9% | 15.4% | 56A |
| 16.4% | 1.4% | 10.0% | 1.9% | 2.2% | 46.4% | 21.8% | 58.6% | 3.3% | 11A-1 |
| 23.7% | 3.3% | 10.5% | 1.9% | 1.8% | 29.9% | 28.9% | 42.2% | 5.2% | 4A-1 |
| 18.7% | 6.9% | 9.2% | 11.9% | 3.2% | 25.2% | 24.9% | 37.5% | 18.8% | 17B |
| 15.4% | 4.2% | 7.3% | 9.5% | 0.9% | 51.2% | 11.6% | 59.3% | 13.7% | ATCC20891 |
| 22.3% | 3.9% | 7.6% | 23.5% | 0.5% | 22.1% | 20.2% | 30.2% | 27.4% | S44 |
| 14.4% | 2.3% | 15.0% | 18.4% | 0.7% | 43.8% | 5.5% | 59.4% | 20.7% | U30 |
| 22.1% | 7.8% | 3.1% | 12.7% | 1.0% | 14.9% | 38.3% | 19.0% | 20.5% | 59A |
| 18.1% | 2.3% | 6.9% | 9.1% | 0.8% | 52.2% | 10.6% | 59.9% | 11.4% | U37-2 |
| 15.8% | 3.9% | 8.8% | 11.6% | 1.2% | 53.3% | 5.5% | 63.3% | 15.5% | S50W |
| 23.7% | 3.8% | 6.3% | 6.9% | 0.6% | 43.0% | 15.6% | 50.0% | 10.7% | ATCC20891 |
| 10.0% | 0.0% | 0.0% | 0.0% | 0.0% | 0.0% | 90.0% | 0.0% | 0.0% | UX |
| 16.6% | 6.3% | 11.9% | 13.3% | 1.7% | 43.0% | 7.3% | 56.6% | 19.5% | LW9 |
| 17.3% | 2.3% | 8.4% | 11.4% | 0.7% | 53.6% | 6.5% | 62.6% | 13.6% | C32-2 |
| 23.8% | 1.2% | 6.4% | 2.5% | 1.9% | 34.4% | 29.8% | 42.6% | 3.7% | 5A-1 |

TABLE 3-continued

LIST OF STRAINS AND COMPOSITIONS UNDER STANDARD SCREENING CONDITIONS

| PERCENT OF TOTAL FATTY ACIDS | | | | | | | Total | Total | |
|---|---|---|---|---|---|---|---|---|---|
| C16:0 | C20:4w6 | C20:5w3 | C22:5w6 | C22:5w3 | C22:6w3 | Other FA | Omega3 | Omega6 | Strain |
| 17.1% | 5.2% | 11.1% | 7.6% | 2.2% | 27.2% | 29.6% | 40.4% | 12.9% | BG1 |
| 25.4% | 2.2% | 9.6% | 7.0% | 1.1% | 46.0% | 8.8% | 56.7% | 9.1% | U3 |
| 16.9% | 12.0% | 6.6% | 16.2% | 0.4% | 25.1% | 22.8% | 32.1% | 28.2% | 55B |
| 26.3% | 2.6% | 8.6% | 2.0% | 2.5% | 32.4% | 25.5% | 43.5% | 4.6% | 18A |
| 19.4% | 0.3% | 9.8% | 0.0% | 0.3% | 38.4% | 31.7% | 48.6% | 0.3% | 32B |
| 16.0% | 16.7% | 8.6% | 18.4% | 0.0% | 22.5% | 17.7% | 31.1% | 35.1% | 56B |
| 18.6% | 7.7% | 11.4% | 3.6% | 4.3% | 31.7% | 22.7% | 47.4% | 11.2% | SX2 |
| 17.8% | 4.4% | 16.2% | 6.4% | 3.7% | 33.6% | 17.8% | 53.5% | 10.9% | 53B |
| 16.8% | 2.7% | 13.8% | 20.5% | 1.4% | 39.3% | 5.5% | 54.4% | 23.3% | S49 |
| 20.8% | 8.0% | 8.9% | 6.4% | 1.7% | 33.9% | 20.3% | 44.5% | 14.4% | S3 |
| 14.8% | 0.3% | 3.7% | 3.9% | 0.0% | 69.9% | 7.4% | 73.6% | 4.2% | 3A-1 |
| 28.1% | 5.2% | 12.7% | 3.2% | 0.9% | 20.9% | 29.0% | 34.5% | 8.4% | 15A |
| 20.9% | 0.7% | 8.5% | 1.0% | 0.0% | 35.8% | 33.0% | 44.3% | 1.7% | 9A-1 |
| 15.7% | 10.2% | 8.8% | 13.4% | 1.5% | 23.9% | 26.3% | 34.3% | 23.7% | 51B |
| 16.2% | 11.2% | 7.8% | 16.4% | 1.5% | 20.4% | 26.5% | 29.7% | 27.6% | 8A-1 |
| 20.5% | 5.5% | 8.6% | 4.8% | 2.7% | 28.7% | 29.2% | 40.0% | 10.3% | 13A-1 |
| 16.1% | 13.6% | 11.1% | 16.0% | 0.0% | 28.4% | 14.8% | 39.4% | 29.6% | 24B-2 |
| 16.9% | 7.3% | 16.4% | 6.1% | 0.0% | 40.8% | 12.4% | 57.2% | 13.4% | 24B-1 |
| 16.2% | 0.0% | 10.9% | 1.0% | 0.0% | 56.5% | 15.5% | 67.4% | 1.0% | 3B |
| 17.0% | 0.0% | 5.0% | 2.3% | 0.0% | 73.4% | 2.3% | 78.3% | 2.3% | SBG5 |
| 20.8% | 4.5% | 5.8% | 3.8% | 1.0% | 22.7% | 41.3% | 29.5% | 8.4% | 16B |
| 19.0% | 14.0% | 8.3% | 18.9% | 0.7% | 23.9% | 15.2% | 32.9% | 32.9% | 6A-1 |
| 18.0% | 0.3% | 10.1% | 0.0% | 0.0% | 48.9% | 22.7% | 59.0% | 0.3% | 33B |
| 16.7% | 5.5% | 14.8% | 8.5% | 1.7% | 31.8% | 21.0% | 48.3% | 13.9% | B40 |
| 15.0% | 1.0% | 11.7% | 2.1% | 0.9% | 62.3% | 6.9% | 74.9% | 3.1% | 28A |
| 17.8% | 18.5% | 8.1% | 20.5% | 0.0% | 22.1% | 12.9% | 30.2% | 39.0% | 43B |
| 16.9% | 0.0% | 3.4% | 2.7% | 0.0% | 61.2% | 15.8% | 64.6% | 2.7% | 1A-1 |
| 15.6% | 2.7% | 11.4% | 10.9% | 0.8% | 53.7% | 4.9% | 65.9% | 13.6% | U41-2 |
| 16.5% | 0.7% | 3.9% | 3.9% | 0.0% | 68.4% | 6.7% | 72.2% | 4.6% | 56B |
| 14.4% | 0.9% | 10.9% | 2.5% | 1.0% | 66.4% | 3.8% | 78.3% | 3.4% | 46A |
| 17.6% | 0.0% | 2.4% | 3.3% | 0.0% | 66.3% | 10.4% | 68.7% | 3.3% | 15A-1 |
| 25.0% | 0.0% | 3.3% | 0.0% | 1.4% | 53.2% | 17.1% | 57.9% | 0.0% | 13A |
| 16.1% | 13.4% | 9.3% | 13.6% | 0.0% | 32.3% | 15.3% | 41.6% | 27.0% | 37B |
| 16.5% | 9.1% | 13.2% | 6.7% | 0.0% | 38.9% | 15.6% | 52.1% | 15.9% | 43B |
| 16.1% | 12.4% | 12.0% | 15.7% | 0.8% | 30.5% | 12.5% | 43.3% | 28.1% | 17B |
| 13.8% | 0.8% | 11.5% | 2.8% | 0.0% | 67.0% | 4.1% | 78.6% | 3.6% | 27A |
| 17.5% | 18.6% | 9.0% | 19.5% | 0.0% | 21.7% | 13.7% | 30.7% | 38.1% | 46B |
| 21.4% | 1.4% | 18.9% | 0.0% | 5.0% | 43.5% | 9.9% | 67.3% | 1.4% | ATCC20890 |
| 17.7% | 0.0% | 0.6% | 4.4% | 0.0% | 68.2% | 9.1% | 68.8% | 4.4% | 5A |
| 17.6% | 16.0% | 9.6% | 18.8% | 0.0% | 25.6% | 12.4% | 35.2% | 34.8% | 28B-2 |
| 14.0% | 0.9% | 13.2% | 1.6% | 0.0% | 64.7% | 5.5% | 77.9% | 2.6% | 27B |
| 19.5% | 2.9% | 16.6% | 1.1% | 1.6% | 30.2% | 28.1% | 48.5% | 4.0% | 49B |
| 17.2% | 0.7% | 6.8% | 2.7% | 0.0% | 63.0% | 9.6% | 69.8% | 3.4% | 18B |
| 14.4% | 3.5% | 13.5% | 26.0% | 1.0% | 37.2% | 4.4% | 51.6% | 29.5% | S49-2 |
| 16.1% | 2.2% | 15.7% | 21.6% | 0.0% | 36.7% | 7.8% | 52.4% | 23.7% | 20B |
| 17.3% | 4.7% | 14.3% | 7.2% | 2.9% | 30.2% | 23.5% | 47.3% | 11.9% | 8B |
| 11.5% | 3.3% | 11.3% | 6.5% | 1.1% | 59.9% | 6.5% | 72.2% | 9.8% | 13B |
| 16.6% | 0.7% | 10.7% | 1.6% | 0.0% | 59.7% | 10.8% | 70.4% | 2.2% | 26A |
| 16.1% | 3.3% | 13.5% | 23.8% | 0.0% | 38.7% | 4.7% | 52.2% | 27.1% | S42 |
| 15.6% | 0.6% | 12.1% | 0.0% | 0.0% | 60.2% | 11.5% | 72.3% | 0.6% | 35B |
| 19.5% | 0.0% | 1.4% | 3.4% | 0.0% | 66.6% | 9.1% | 68.0% | 3.4% | 42A |
| 18.9% | 3.5% | 12.7% | 25.0% | 0.0% | 35.0% | 5.0% | 47.6% | 28.5% | 40A |
| 25.2% | 3.3% | 9.3% | 21.8% | 0.0% | 30.3% | 10.1% | 39.6% | 25.1% | S50C |
| 17.6% | 11.1% | 13.2% | 14.1% | 1.3% | 28.7% | 14.0% | 43.2% | 25.2% | 59A |
| 19.9% | 0.0% | 5.5% | 1.9% | 0.0% | 66.8% | 6.0% | 72.3% | 1.9% | SBG9 |
| 15.4% | 3.1% | 13.2% | 26.1% | 0.0% | 35.8% | 6.5% | 49.1% | 29.1% | 21B |
| 18.9% | 0.7% | 11.6% | 0.0% | 0.0% | 59.1% | 9.7% | 70.7% | 0.7% | 2B |
| 14.1% | 1.1% | 12.4% | 2.0% | 0.0% | 65.2% | 5.2% | 77.6% | 3.1% | 1B |
| 22.2% | 16.2% | 6.3% | 17.7% | 0.0% | 18.1% | 19.5% | 24.4% | 33.8% | 55B |
| 16.0% | 1.0% | 4.5% | 0.0% | 0.0% | 69.5% | 9.0% | 74.0% | 1.0% | 3A |
| 17.0% | 4.3% | 12.4% | 29.8% | 0.0% | 34.0% | 2.5% | 46.4% | 34.1% | 9B |
| 15.4% | 4.3% | 8.7% | 13.2% | 0.0% | 53.2% | 5.1% | 62.0% | 17.5% | U24 |
| 14.2% | 3.1% | 12.0% | 20.0% | 1.1% | 35.2% | 14.3% | 48.3% | 23.2% | U28 |
| 16.8% | 14.6% | 10.1% | 16.0% | 0.6% | 27.7% | 14.0% | 38.5% | 30.7% | 28B-1 |
| 23.2% | 1.9% | 8.3% | 1.1% | 2.3% | 22.7% | 40.4% | 33.3% | 3.0% | 44B |
| 24.6% | 15.8% | 8.7% | 16.0% | 0.0% | 15.3% | 19.6% | 24.0% | 31.8% | 54B |
| 15.5% | 0.0% | 1.3% | 2.9% | 0.0% | 72.7% | 7.6% | 74.0% | 2.9% | 55A |
| 18.4% | 1.0% | 5.0% | 3.0% | 0.0% | 66.2% | 6.4% | 71.3% | 3.9% | 49A |
| 18.6% | 15.3% | 9.4% | 18.0% | 0.0% | 27.3% | 11.4% | 36.7% | 33.3% | 51A |
| 23.5% | 13.1% | 7.3% | 17.9% | 0.0% | 26.7% | 11.4% | 34.0% | 31.0% | 14A-1 |
| 13.3% | 1.1% | 14.5% | 0.9% | 0.0% | 64.6% | 5.6% | 79.1% | 2.0% | 25B |
| 22.9% | 2.4% | 10.3% | 21.5% | 0.0% | 26.5% | 16.4% | 36.9% | 23.9% | 41A |
| 16.8% | 1.0% | 9.7% | 2.7% | 0.0% | 58.3% | 11.5% | 68.0% | 3.7% | 24A |

TABLE 3-continued

LIST OF STRAINS AND COMPOSITIONS UNDER STANDARD SCREENING CONDITIONS

| PERCENT OF TOTAL FATTY ACIDS | | | | | | | Total | Total | |
|---|---|---|---|---|---|---|---|---|---|
| C16:0 | C20:4w6 | C20:5w3 | C22:5w6 | C22:5w3 | C22:6w3 | Other FA | Omega3 | Omega6 | Strain |
| 0.4% | 8.5% | 14.1% | 10.2% | 2.1% | 27.6% | 37.0% | 43.8% | 18.8% | 61A |
| 30.5% | 0.0% | 7.1% | 0.0% | 0.0% | 0.6% | 61.8% | 7.7% | 0.0% | BRBG |
| 18.2% | 14.9% | 8.3% | 18.7% | 0.0% | 24.4% | 15.5% | 32.7% | 33.6% | 17A |
| 17.4% | 2.0% | 9.3% | 2.8% | 0.0% | 55.7% | 12.7% | 65.0% | 4.9% | 60A |
| 14.1% | 0.8% | 13.0% | 1.2% | 0.0% | 67.8% | 3.1% | 80.8% | 2.0% | 26B |
| 17.8% | 5.0% | 6.9% | 15.0% | 1.5% | 47.4% | 6.4% | 55.8% | 20.0% | ATCC20888 |
| 16.0% | 0.0% | 1.8% | 2.0% | 0.0% | 70.8% | 9.4% | 72.6% | 2.0% | 2A |
| 24.6% | 0.0% | 4.0% | 0.0% | 0.0% | 49.4% | 22.0% | 53.4% | 0.0% | 44A |
| 17.4% | 1.8% | 0.0% | 2.9% | 0.0% | 55.3% | 23.3% | 55.3% | 4.6% | 14A |
| 23.3% | 1.3% | 4.6% | 0.0% | 0.0% | 12.6% | 58.1% | 17.3% | 1.3% | 41B |
| 19.3% | 0.0% | 1.1% | 3.8% | 0.0% | 66.6% | 9.1% | 67.8% | 3.8% | 66A |
| 18.6% | 15.6% | 8.3% | 17.1% | 1.1% | 24.6% | 14.8% | 33.9% | 32.7% | 11A |
| 19.6% | 5.1% | 10.1% | 27.2% | 0.0% | 27.5% | 10.6% | 37.5% | 32.3% | 2X |
| 15.7% | 2.4% | 14.0% | 25.7% | 0.0% | 36.7% | 5.4% | 50.8% | 28.1% | 33A |
| 14.6% | 1.5% | 13.5% | 0.0% | 0.0% | 66.0% | 4.3% | 79.5% | 1.5% | ATCC20892 |
| PRIOR STRAINS | | | | | | | | | |
| 15.7% | 3.9% | 3.7% | 8.1% | 0.0% | 55.1% | 13.5% | 58.8% | 12.0% | ATCC34304 |
| 28.2% | 1.6% | 6.9% | 11.4% | 0.0% | 17.8% | 34.1% | 24.7% | 12.9% | ATCC24473 |
| 15.2% | 2.9% | 7.7% | 9.8% | 0.6% | 54.6% | 9.2% | 62.9% | 12.7% | ATCC28211 |
| 23.2% | 10.7% | 4.3% | 12.6% | 1.5% | 20.6% | 27.0% | 26.4% | 23.4% | ATCC28209 |
| 13.2% | 6.3% | 6.9% | 4.3% | 0.0% | 60.1% | 9.1% | 67.0% | 10.6% | ATCC28210 |

TABLE 4

COMPOSITION OF OMEGA 3 FATTY ACID FRACTION

| EPA C20:5w3 | DPA C22:5w3 | DHA C22:6w3 | Strain |
|---|---|---|---|
| 44.0% | 1.1% | 54.9% | 21 |
| 4.6% | 0.9% | 94.5% | ATCC20889 |
| 19.3% | 0.7% | 80.0% | U40-2 |
| 31.9% | 0.0% | 68.1% | 21B |
| 87.9% | 0.0% | 12.1% | BRBG1 |
| 12.5% | 6.1% | 81.5% | 56A |
| 17.0% | 3.7% | 79.3% | 11A-1 |
| 24.9% | 4.3% | 70.8% | 4A-1 |
| 24.4% | 8.4% | 67.2% | 17B |
| 12.2% | 1.5% | 86.3% | ATCC20891 |
| 25.1% | 1.7% | 73.2% | S44 |
| 25.2% | 1.1% | 73.7% | U30 |
| 16.2% | 5.4% | 78.4% | 59A |
| 11.5% | 1.4% | 87.1% | U37-2 |
| 14.0% | 1.9% | 84.2% | S50W |
| 12.7% | 1.3% | 86.0% | ATCC20891 |
| — | — | — | UX |
| 21.0% | 2.9% | 76.1% | LWN9 |
| 13.4% | 1.0% | 85.6% | C32-2 |
| 15.0% | 4.3% | 80.7% | 5A-1 |
| 27.4% | 5.4% | 67.2% | BRBG1 |
| 17.0% | 1.9% | 81.1% | U3 |
| 20.5% | 1.3% | 78.2% | 55B |
| 19.8% | 5.8% | 74.4% | 18A |
| 20.1% | 0.7% | 79.2% | 32B |
| 27.8% | 0.0% | 72.2% | 56B |
| 24.1% | 9.1% | 66.9% | SX2 |
| 30.3% | 6.9% | 62.8% | 53B |
| 25.3% | 2.5% | 72.2% | S49 |
| 19.9% | 3.8% | 76.3% | S3 |
| 5.0% | 0.0% | 95.0% | 3A-1 |
| 36.9% | 2.6% | 60.5% | 15A |
| 19.3% | 0.0% | 80.7% | 9A-1 |
| 25.8% | 4.4% | 69.8% | 51B |
| 26.3% | 5.0% | 68.7% | 8A-1 |
| 21.6% | 6.7% | 71.7% | 13A-1 |
| 28.0% | 0.0% | 72.0% | 24B-2 |
| 28.7% | 0.0% | 71.3% | 24B-1 |
| 16.2% | 0.0% | 83.8% | 3B |
| 6.3% | 0.0% | 93.7% | SBG5 |
| 19.7% | 3.3% | 77.0% | 16B |
| 25.2% | 2.1% | 72.6% | 6A-1 |
| 17.1% | 0.0% | 82.9% | 33B |
| 30.5% | 3.6% | 65.9% | B40 |
| 15.6% | 1.2% | 83.1% | 28A |
| 26.8% | 0.0% | 73.2% | 43B |
| 5.2% | 0.0% | 94.8% | 1A-1 |
| 17.4% | 1.2% | 81.5% | U41-2 |
| 5.4% | 0.0% | 94.6% | 56B |
| 13.9% | 1.3% | 84.8% | 46A |
| 3.5% | 0.0% | 96.5% | 15A-1 |
| 5.8% | 2.4% | 91.8% | 13A |
| 22.3% | 0.0% | 77.7% | 37B |
| 25.4% | 0.0% | 74.6% | 43B |
| 27.7% | 1.9% | 70.3% | 17B |
| 14.7% | 0.0% | 85.3% | 27A |
| 29.2% | 0.0% | 70.8% | 46B |
| 28.0% | 7.5% | 64.5% | ATCC20890 |
| 0.9% | 0.0% | 99.1% | 5A |
| 27.3% | 0.0% | 72.7% | 28B-2 |
| 16.9% | 0.0% | 83.1% | 27B |
| 34.3% | 3.4% | 62.3% | 49B |
| 9.7% | 0.0% | 90.3% | 18B |
| 26.1% | 1.9% | 71.9% | S49-2 |
| 29.9% | 0.0% | 70.1% | 20B |
| 30.1% | 6.2% | 63.7% | 8B |
| 15.6% | 1.5% | 82.9% | 13B |
| 15.2% | 0.0% | 84.8% | 26A |
| 25.9% | 0.0% | 74.1% | S42 |
| 16.7% | 0.0% | 83.3% | 35B |
| 2.1% | 0.0% | 97.9% | 42A |
| 26.6% | 0.0% | 73.4% | 40A |
| 23.4% | 0.0% | 76.6% | S50C |
| 30.6% | 2.9% | 66.4% | 59A |
| 7.6% | 0.0% | 92.4% | SBG9 |
| 27.0% | 0.0% | 73.0% | 21B |
| 16.4% | 0.0% | 83.6% | 2B |
| 15.9% | 0.0% | 84.1% | 1B |
| 25.9% | 0.0% | 74.1% | 55B |
| 6.0% | 0.0% | 94.0% | 3A |
| 26.7% | 0.0% | 73.3% | 9B |
| 14.1% | 0.0% | 85.9% | U24 |
| 24.9% | 2.2% | 72.9% | U28 |

TABLE 4-continued

| EPA | DPA | DHA | Strain |
|---|---|---|---|
| 26.4% | 1.5% | 72.1% | 28B-1 |
| 24.8% | 6.9% | 68.3% | 44B |
| 36.4% | 0.0% | 63.6% | 54B |
| 1.8% | 0.0% | 98.2% | 55A |
| 7.1% | 0.0% | 92.9% | 49A |
| 25.6% | 0.0% | 74.4% | 51A |
| 21.5% | 0.0% | 78.5% | 14A-1 |
| 18.4% | 0.0% | 81.6% | 25B |
| 28.1% | 0.0% | 71.9% | 41A |
| 14.3% | 0.0% | 85.7% | 24A |
| 32.3% | 4.8% | 63.0% | 61A |
| 91.6% | 0.0% | 8.4% | BRBG |
| 25.5% | 0.0% | 74.5% | 17A |
| 14.4% | 0.0% | 85.6% | 60A |
| 16.1% | 0.0% | 83.9% | 26B |
| 12.4% | 2.7% | 84.9% | ATCC20888 |
| 2.5% | 0.0% | 97.5% | 2A |
| 7.5% | 0.0% | 92.5% | 44A |
| 0.0% | 0.0% | 100.0% | 14A |
| 26.7% | 0.0% | 73.3% | 41B |
| 1.7% | 0.0% | 98.3% | 66A |
| 24.5% | 3.1% | 72.4% | 11A |
| 26.8% | 0.0% | 73.2% | 2X |
| 27.6% | 0.0% | 72.4% | 33A |
| 17.0% | 0.0% | 83.0% | ATCC20892 |

PRIOR STRAINS

| EPA C20:5w3 | DPA C22:5w3 | DHA C22:6w3 | Strain |
|---|---|---|---|
| 6.4% | 0.0% | 93.6% | ATCC34304 |
| 27.9% | 0.0% | 72.1% | ATCC24473 |
| 12.2% | 1.0% | 86.8% | ATCC28211 |
| 16.4% | 5.6% | 78.1% | ATCC28209 |
| 10.3% | 0.0% | 89.7% | ATCC28210 |

Example 6

Enhanced growth rates of strains isolated by method in Example 1 compared to ATCC strains (previously known strains)

Figure 5:
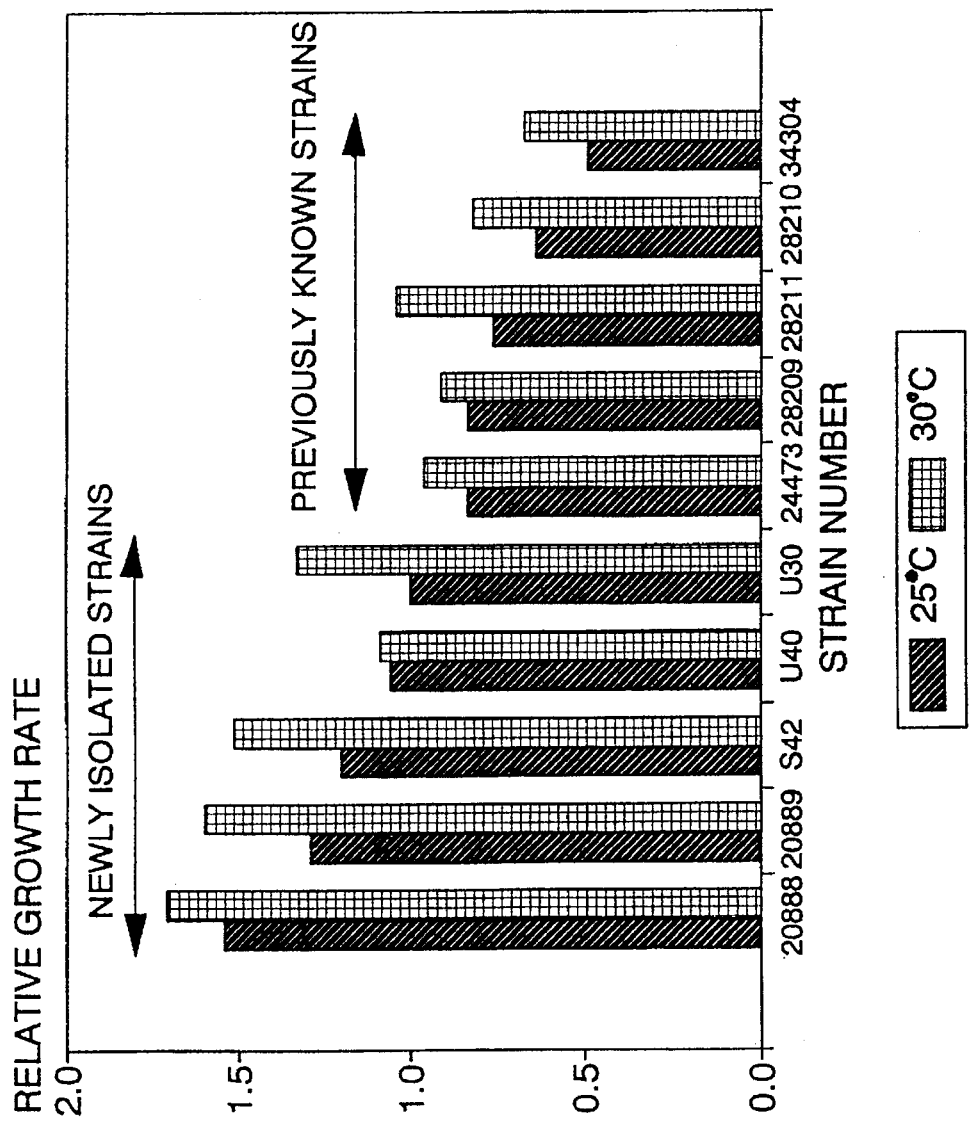
FIG. 5 is a graph showing growth of various newly isolated strains of the invention and previously isolated strains, at 25° C. and at 30° C. Growth rates are normalized to the growth rate of strain U-30 at 25° C. Previously isolated strains are designated by their ATCC accession numbers. Numerical data in terms of cell number doublings per day are given in Table 5.

Cells of Schizochytrium sp. S31 (ATCC No. 20888), Schizochytrium sp. S8 (ATCC No. 20889), Thraustochytrium sp. S42, Thraustochytrium sp. U42-2, Thraustochytrium sp. S42 and U30, (all isolated by the method of Example 1) and Thraustochytrium aureum (ATCC #28211) and Schizochytrium aggregatum (ATCC #28209) (previously known strains) were picked from solid F-1 medium and placed into 50 ml of M-5 medium. This medium consists of (on a per liter basis): Yeast Extract, 1 g; NaCl, 25 g; MgSO$_4$·7H$_2$O, 5 g; KCl, 1 g; CaCl$_2$, 200 mg; glucose, 5 g; glutamate, 5 g; KH$_2$PO$_4$, 1 g; PII metals, 5 ml; A-vitamins solution, 1 ml; and antibiotic solution, 1 ml. The pH of the solution was adjusted to 7.0 and the solution was filter sterilized. After three days of growth on an orbital shaker (200 rpm, 27° C.), 1–2 ml of each culture was transferred to another flask of M-5 medium and placed on the shaker for 2 days. The cultures (1–2 ml) were then transferred to another flask of M-5 medium and placed on the shaker for 1 day. This process ensured that all cultures were in the exponential phase of growth. These later cultures were then used to inoculate two 250 ml flasks of M-5 medium for each strain. These flasks were than placed on shakers at 25° C. and 30° C., and changes in their optical density were monitored on a Beckman DB-G spectrophotometer (660 nm, 1 cm path length). Optical density readings were taken at the following times: 0, 6, 10, 14, 17.25, 20.25 and 22.75 hours. Exponential growth rates (doublings/day) were then calculated from the optical density data by the method of Sorokin (1973). The results are presented in Table 5 and illustrated (normalized to the growth of strain U30 at 25° C.) in FIG. 5. The data indicate that the strains isolated by the method in Example 1 have much higher growth rates than the previously known ATCC strains at both 25° C. and 30° C., even under the optimized phosphate levels essential for continuous growth. Strains of Thraustochytriales isolated from cold Antarctic waters have not been shown to grow at 30° C.

TABLE 5

| | Exponential Growth Rate (doublings/day) | |
|---|---|---|
| Strain | 25° C. | 30° C. |
| S31* | 8.5 | 9.4 |
| U40-2* | 5.8 | 6.0 |
| S8* | 7.1 | 8.8 |
| S42* | 6.6 | 8.3 |
| U30* | 5.5 | 7.3 |
| 28209** | 4.6 | 5.0 |
| 28210** | 3.5 | 4.5 |
| 28211** | 4.2 | 5.7 |
| 34304** | 2.7 | 3.7 |
| 24473** | 4.6 | 5.3 |

*strain isolated by method in Example 1
**previously known ATCC strain

Example 7

Enhanced production characteristics (growth and lipid induction) of strains isolated by method in Example 1 compared to ATCC strains (prior art strains)

Figure 6:
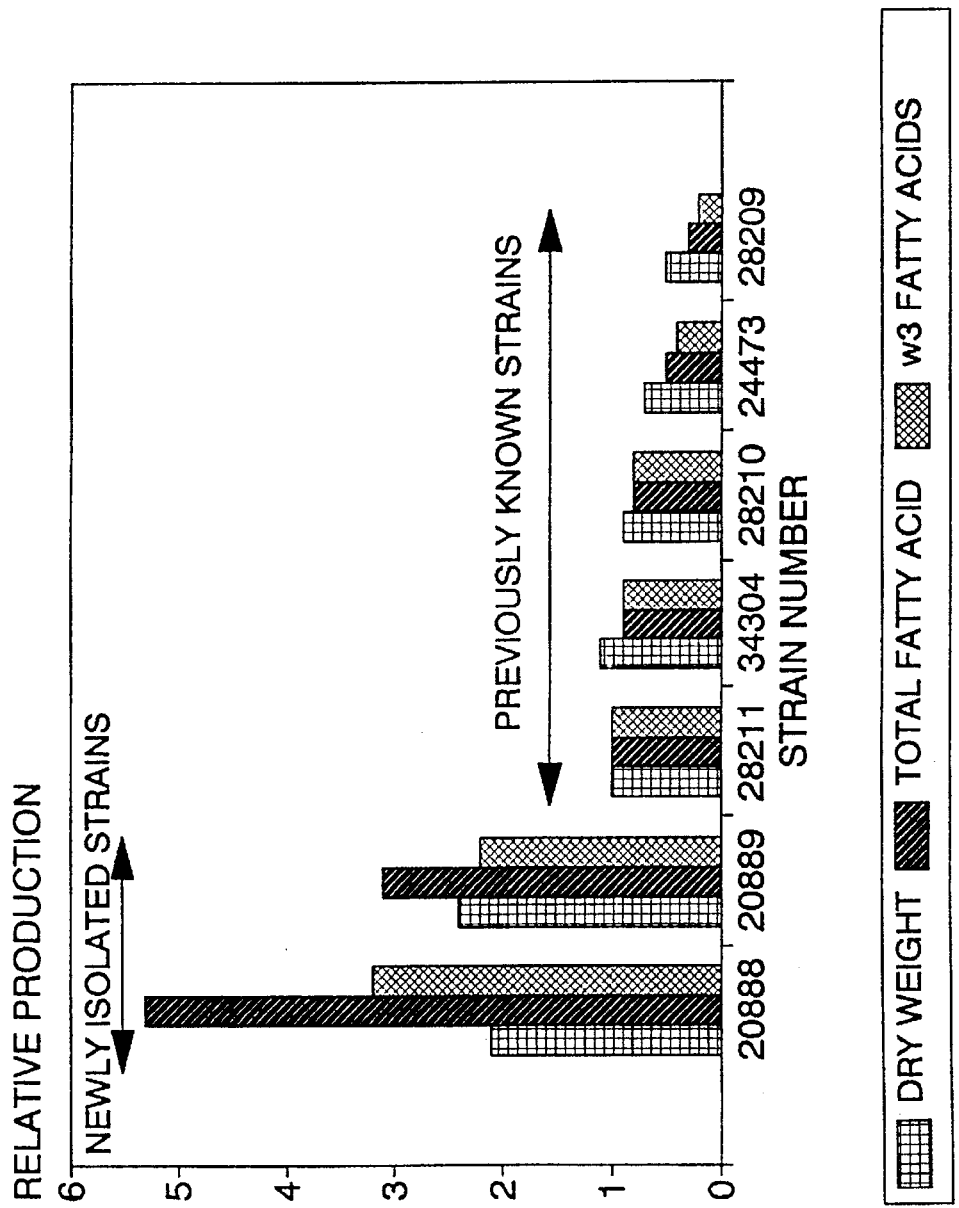
FIG. 6 is a graph of total yields of cellular production after induction by nitrogen limitation. Each of ash-free dry weight, total fatty acids and omega-3 highly unsaturated fatty acids, as indicated, was plotted, normalized to the corresponding value for strain 28211. All strains are identified by ATCC accession numbers.

Cells Schizochytrium sp. S31 (ATCC No. 20888), Schizochytrium sp. S8 (ATCC No. 20889) (both isolated by the method of Example 1) and Thraustochytrium aureum (ATCC #2821 L) and Schizochytrium aggregatum (ATCC #28209) (prior art strains) were picked from solid F-1 medium and placed into 50 ml of M-5 medium (see Example 5 ). The pH of the solution was adjusted to 7.0 and the solution was filter sterilized. After three days of growth on an orbital shaker (200 rpm, 27° C.), 1–2 ml of each culture was transferred to another flask of M-5 medium and placed on the shaker for 2 days. The ash-free dry weights for each of these cultures were then quickly determined that 3.29 mg of each culture was pipetted into two 250 ml erlenmeyer flasks containing 50 ml of M-5 medium. These flasks were placed on a rotary shaker (200 rpm, 27° C.). After 24 hours 20 ml portions of each culture were then centrifuged, the supernatants discarded, and the cells transferred to 250 ml erlenmeyer flasks containing 50 ml of M-5 medium without any glutamate (N-source). The flasks were placed back on the shaker, and after another 12 hours they were sampled to determine ash-free dry weights and quantify fatty acid contents by the method of Lepage and Roy (1984). The results are illustrated (normalized to the yields of ATCC No. 28211, previously known strain) in FIG. 6. The results indicate that the strains isolated by the method of Example 1 produced 2–3 times as much ash-free dry weight in the same period of time, under a combination of exponential growth and nitrogen limitation (for lipid induction) as the prior art ATCC strains. In addition, higher yields of total fatty acids and omega-3 fatty acids were obtained from strains of the present invention with strains S31 (ATCC No. 20888) producing 3–4 times as much omega-3 fatty acids as the prior art ATCC strains.

Example 8

Enhanced salinity tolerance and fatty acid production by strains isolated by method in Example 1

Figure 7:
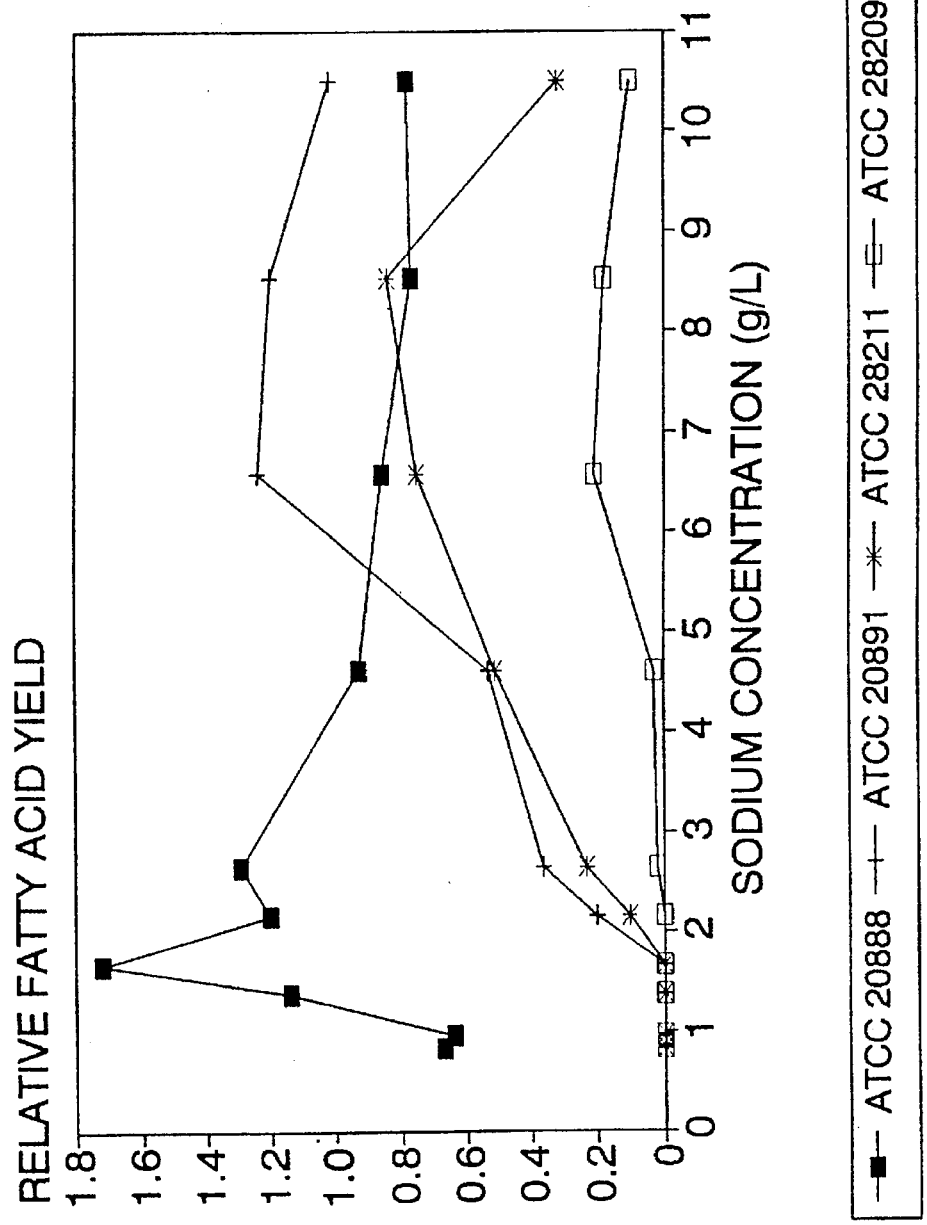
FIG. 7 is a graph of fatty acid yields after growth in culture media having the salinity indicated on the abscissa. Strains shown are newly isolated strains S31 (ATCC 20888) (□) and U42-2 (KTCC 20891) (+) and previously isolated strains, ATCC 28211 (◊) and ATCC 28209 (△). Fatty acid yields are plotted as relative yields normalized to an arbitrary value of 1.00 based on the average growth rate exhibited by S31 (ATCC 20888) (□) over the tested salinity range.

Strains of 4 species of Oomycetes, Schizochytrium sp. S31 (ATCC No. 20888) and Thraustochytrium sp. U42-2 (ATCC No. 20891) (both isolated and screened by the method of Example 1), and S. aggregatum (ATCC 28209) and T. aureum (ATCC 28210) (obtained from the American Type Culture Collection) were picked from solid F-1 medium and incubated for 3–4 days at 27° C. on a rotary shaker (200 rpm). A range of differing salinity medium was prepared by making the following dilutions of M medium salts (NaCl, 25 g/l; $MgSO_4.7H_2O$, 5 g/l; KCl, 1 g/l; $CaCl_2$, 200 mg/l: 1) 100% (w/v M medium salts; 2) 80% (v/v) M medium, 20% (v/v) distilled water; 3) 60% (v/v) M medium, 40% (v/v) distilled water; 4) 40% (v/v) M medium, 60% (v/v) distilled water; 5) 20% (v/v) M medium, 80% distilled water; 6) 15% (v/v) M medium, 85% (v/v) distilled water; 7) 10% (v/v) M medium, 90% (v/v) distilled water; 8) 7% (v/v) M medium, 93% (v/v) distilled water; 9) 3% (v/v) M medium, 97% (v/v) distilled water; 10) 1.5% (v/v) M medium, 98.5% (v/v) distilled water. The following nutrients were added to the treatments (per liter): glucose, 5 g; glutamate, 5 g; yeast ext., 1 g; $(NH_4)_2SO_4$, 200 mg; $NaHCO_3$, 200 mg; PII metals, 5 ml; A-vitamins solution, 1 ml; and antibiotics solution, 2 ml. Fifty ml of each of these treatments were inoculated with 1 ml of the cells growing in the F-1 medium. These cultures were placed on an orbital shaker (200 rpm) and maintained at 27° C. for 48 hr. The cells were harvested by centrifugation and total fatty acids determined by gas chromatography. The results are illustrated in FIG. 7. Thraustochytrium sp. U42-2 (ATCC No. 20891) isolated by the method of Example 1 can yield almost twice the amount of fatty acids produced by T. aureum (ATCC 28210) and over 8 times the amount of fatty acids produced by S. aggregatum (ATCC 28209). Additionally, U42-2 appears to have a wider salinity tolerance at the upper end of the salinity range evaluated. Schizochytrium sp. S31 (ATCC No. 20888), also isolated by the method in Example 1, exhibited both a high fatty acid yield (2.5 to 10 times that of the previously known ATCC strains) and a much wider range of salinity tolerance than the ATCC strains. Additionally, Schizochytrium sp. S31 (ATCC No. 20888) grows best at very low salinities. This property provides a strong economic advantage when considering commercial production, both because of the corrosive effects of saline waters on metal reactors, and because of problems associated with the disposal of saline waters.

Example 9

Cultivation/Low Salinity

Fifty ml of M/10-5 culture media in a 250 ml erlenmeyer flask was inoculated with a colony of Schizochytrium sp. S31 (ATCC No. 20888) picked from an agar slant. The M/10-5 media contains: 1000 ml deionized water, 2.5 g NaCl, 0.5 g $MgSO_4$ $7H_2O$, 0.1 g KCl, 0.02 g $CaCl_2$, 1.0 g $KH_2PO_4$, 1.0 g yeast extract, 5.0 g glucose, 5.0 g glutamic acids, 0.2 g $NaHCO_3$, 5 ml PII trace metals, 2 ml vitamin mix, and 2 ml antibiotic mix. The culture was incubated at 30° C. on a rotary shaker (200 rpm). After 2 days the culture was at a moderate density and actively growing. 20 ml of this actively growing culture was used to inoculate a 2 liter fermenter containing 1700 ml of the same culture media except the concentration of the glucose and glutamate had been increased to 40 g/l (M/10-40 media). The fermente, was maintained at 30° C., with aeration at 1 vol/vol/min, and mixing at 300 rpm. After 48 hr, the concentration of cells in the fermenter was 21.7 g/l. The cells were harvested by centrifugation, lyophilized, and stored under $N_2$.

The total fatty acid content and omega-3 fatty acid content was determined by gas chromatography. The total fatty acid content of the final product was 39.0% ash-free dry weight. The omega-3 highly unsaturated fatty acid content (C20:5w3, C22:5w3 and C22:6w3) of the microbial product was 25.6% of the ash-free dry weight. The ash content of the sample was 7.0%.

Example 10

Growth and gas chromatographic analysis of fatty acid production by various strains as described in example 5 revealed differences in fatty acid diversity. Strains of the present invention synthesized fewer different fatty acids than previously available strains. Lower diversity of fatty acids is advantageous in fatty acid purification since there are fewer impurities to be separated. For food supplement purposes, fewer different fatty acids is advantageous because the likelihood of ingesting unwanted fatty acids is reduced. Table 6 shows the number of different highly unsaturated fatty acids present, at concentrations greater than 1% by weight of total fatty acids for previously known strains, designated by ATCC number and various strains of the present invention.

TABLE 6

| Strain | No. of Different Fatty Acids at 1% or Greater % of Total Fatty Acids |
|---|---|
| 34304** | 8 |
| 28211** | 8 |
| 24473** | 10 |
| 28209** | 13 |
| 28210** | 8 |
| S31* | 5 |
| S8* | 6 |
| 79B* | 6 |

*strain isolated by the method in Example 1
**previously known ATCC strain

Example 11

Recovery

Fifty ml of M5 culture media in a 250 ml erlenmeyer flask was inoculated with a colony of Schizochytrium sp. S31 (ATCC No. 20888) picked from an agar slant. The M5 media contains: 1000 ml deionized water, 25.0 g NaCl, 5.0 g MgSO4.7H2O, 1.0 g KCl, 0.2 g $CaCl_2$, 1.0 g $KH_2PO_4$, 1.0 g yeast extract, 5.0 g glucose, 5.0 g glutamic acid, 0.2 g $NaHCO_3$, 5 ml PII trace metals, 2 ml vitamin mix, and 2 ml antibiotic mix. The culture was incubated at 30° C. on a rotary shaker (200 rpm). After 2 days the culture was at a moderate density and actively growing. 20 ml of this actively growing culture was used to inoculate an 1 liter fermenter containing 1000 ml of the same culture media except the concentration of the glucose and glutamate had been increased to 40 g/l (M20 media). The fermenter was maintain at 30° C. and pH 7.4, with aeration at 1 vol/min, and mixing at 400 rpm. After 48 hr, the concentration of the cells in the fermenter was 18.5 g/l. Aeration and mixing in the fermenter was turned off. Within 2–4 minutes, the cells flocculated and settled in the bottom 250 ml of the fermenter. This concentrated zone of cells had a cell concentration of 72 g/l. This zone of cells can be siphoned from the fermenter, and: (1) transferred to another reactor for a period of nitrogen limitation (e.g., combining the highly concentrated production of several fermenters); or (2) harvested directly by centrifugation or filtration. By preconcentrating the cells in this manner, 60–80% less water has to be processed to recover the cells.

Example 12

Utilization of a variety of carbon and nitrogen sources

Fifty ml of M5 culture media in a 250 ml erlenmeyer flask was inoculated with a colony of Schizochytrium sp. S31 (ATCC No. 20888) or Thraustochytrium sp. U42-2 (ATCC No. 20891) picked from an agar slant. The M5 media was described in Example 4 except for 2 ml vitamin mix, and 2 ml antibiotic mix. The culture was incubated at 30° C. on a rotary shaker (200 rpm). After 2 days the culture was at a moderate density and actively growing. This culture was used to inoculate flasks of M5 media with one of the following substituted for the glucose (at 5 g/l): dextrin, sorbitol, fructose, lactose, maltose, sucrose, corn starch, wheat starch, potato starch, ground corn; or one of the following substituted for the glutamate (at 5 g/l): gelysate, peptone, tryptone, casein, corn steep liquor, urea, nitrate, ammonium, whey, or corn gluten meal. The cultures were incubated for 48 hours on a rotary shaker (200 rpm, 27° C.). The relative culture densities, representing growth on the different organic substrates, are illustrated in Tables 7–8.

TABLE 7

Utilization of Nitrogen Sources

| N-Source | Thraustochytrium sp. U42-2 ATCC No. 20891 | Schizochytrium sp. S31 ATCC No. 20888 |
| --- | --- | --- |
| glutamate | +++ | +++ |
| gelysate | +++ | +++ |
| peptone | ++ | ++ |
| tryptone | ++ | ++ |
| casein | ++ | ++ |
| corn steep liquor | +++ | +++ |
| urea | + | ++ |
| nitrate | ++ | +++ |
| ammonium | + | +++ |
| whey | +++ | +++ |
| corn gluten meal | +++ | +++ |

+++ = high growth
++ = medium growth
+ = low growth
0 = no growth

TABLE 8

Utilization of Organic Carbon Sources.

| C-Source | Thraustochytrium sp. U42-2 ATCC No. 20891 | Schizochytrium sp. S31 ATCC No. 20888 |
| --- | --- | --- |
| glucose | +++ | +++ |
| dextrin | +++ | +++ |
| sorbitol | + | + |
| fructose | + | +++ |
| lactose | + | + |
| maltose | +++ | + |
| sucrose | + | + |

TABLE 8-continued

Utilization of Organic Carbon Sources.

| C-Source | Thraustochytrium sp. U42-2 ATCC No. 20891 | Schizochytrium sp. S31 ATCC No. 20888 |
| --- | --- | --- |
| corn starch | +++ | + |
| wheat starch | +++ | + |
| potato starch | +++ | + |
| ground corn | +++ | 0 |

+++ = high growth
++ = medium growth
+ = low growth
0 = no growth

Example 13

Figure 8:
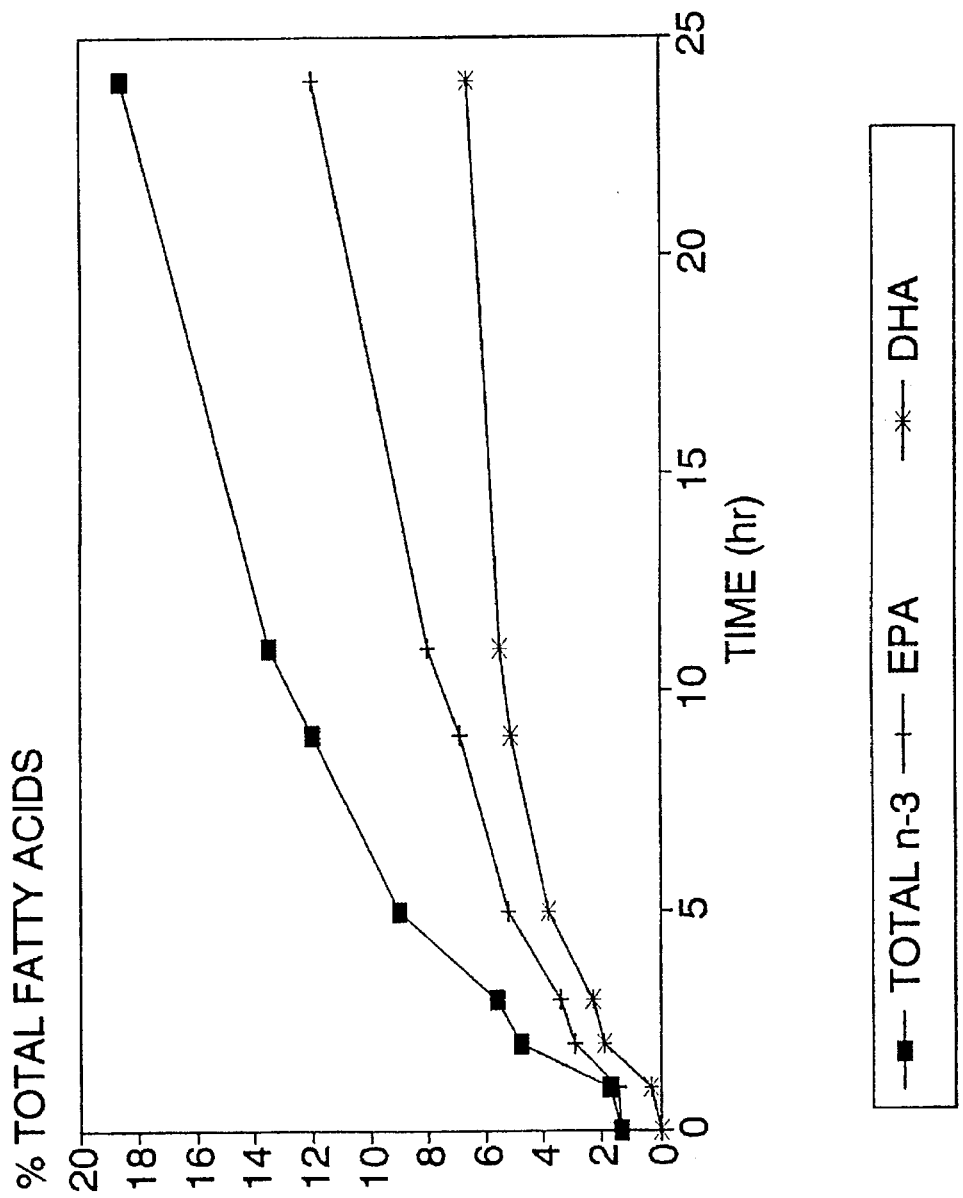
FIG. 8 is a graph of increases in the omega-3 highly unsaturated fatty acid content of the total lipids in the brine shrimp, *Artemia salina*, fed Thraustochytrid strain (ATCC 20890) isolated by the method in Example 1. EPA= C20:5w3; DHA=C22:5w3.
Figure 9:
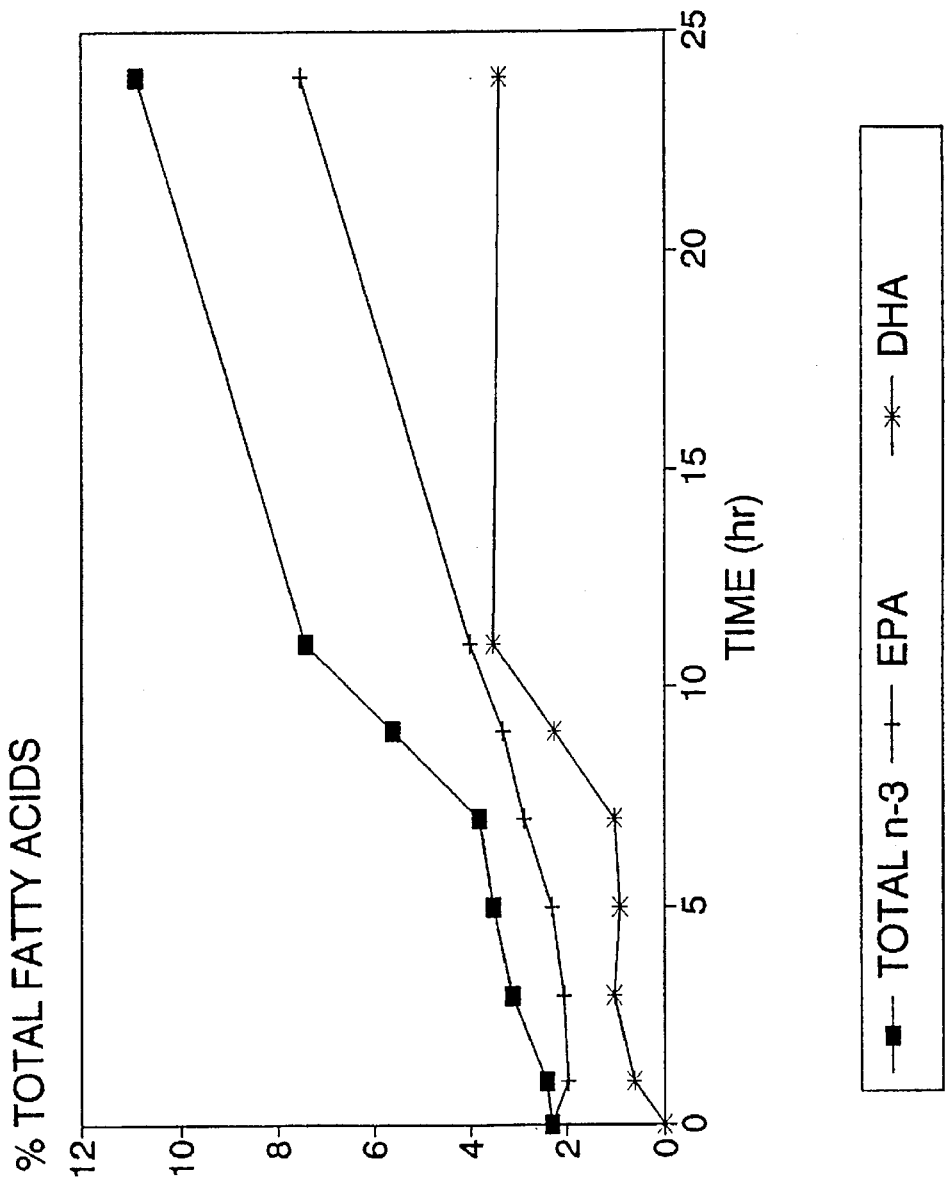
FIG. 9 is a graph of increases in the omega-3 highly unsaturated fatty acid content of the total lipids in the brine shrimp, *Artemia salina*, fed Thraustochytrid strain (ATCC 20888) isolated by the method in Example 1. EPA= C20:5w3; DHA=C22:5w3.

Feeding of thraustochytrid-based feed supplement to brine shrimp to increase their omega-3 HUFA content Cellular biomass of Thraustochytrium sp. 12B (ATCC 20890) was produced in shake flasks in M-5 medium (see Example 6) at 25° C. Cellular biomass of Thraustochytrium sp. S31 (ATCC 20888 ) was produced in shake flasks in M-5/10 medium (see Example 9) at 27° C. The cells of each strain were harvested by centrifugation. The pellet was washed once with distilled water and recentrifuged to produce a 50% solids paste. The resulting paste was resuspended in sea water and then added to an adult brine shrimp culture as a feed supplement. The brine shrimp had previously been reared on agricultural waste products and as a result their omega-3 HUFA content was very low, only 1.3–2.3% of total fatty acids (wild-caught brine shrimp have an average omega-3 HUFA content of 6–8% total fatty acids). The brine shrimp (2–3/mL) were held in a 1 liter beaker filled with sea water and an airstone was utilized to aerate and mix the culture. After addition of the feed supplement, samples of the brine shrimp were periodically harvested, washed, and their fatty acid content determined by gas chromatography. The results are illustrated in FIGS. 8–9. When fed the thraustochytrid-based feed supplement as a finishing feed, the omega-3 content of the brine shrimp can be raised to that of wild-type brine shrimp within 5 hours if fed strain 12B or within 11 hours when fed strain S31. The omega-3 HUFA content of the brine shrimp can be greatly enhanced over that of the wild type if fed these feed supplements for up to 24 hours. Additionally, these feed supplements greatly increase the DHA content of the brine shrimp, which is generally only reported in trace levels in wild-caught brine shrimp.

Example 14

Feeding of thraustochytrid-based feed Supplement to laying hens to produce omega-3 HUFA enriched eggs Cellular biomass of Thraustochytrium sp. S31 (ATCC 20888) was produced in a 10 liter fermenter in M-5/10 medium (see Example 9) at 27° C. The cells of Thraustochytrium sp. S31 (ATCC 20888) were harvested by centrifugation, washed once with distilled water and recentrifuged to produce a 50% solids paste. This cell paste was then treated in one of two ways: 1) lyophilized; or 2) mixed with ground corn to produce a 70% solids paste and then extruded at 90°–120° C. and air dried. The resulting dried products were then ground, analyzed for omega-3 HUFA content, and mixed into layers rations at a level to provide 400 mg of omega-3 HUFA per day to the laying hens (400 mg omega-3 HUFA/100 grams layers ration). The resulting eggs were sampled over a period of approximately 45 days and analyzed by gas chromatography for omega-3 HUFA's. Eggs with up to 200–425 mg omega-3 HUFA's/egg were produced by the hen fed omega-3 supplement. When cooked, these eggs did not exhibit any fishy odors. The control hens produced eggs with only approximately 20 mg omega-3 HUFA/egg. There was no significant difference between the number of eggs laid by the control group and the hen fed the omega-3 supplement. There was also no different in the color of yolks of the eggs produced with the feed supplement and the control diet.

Example 15

Production of high purity (>90% purity omega-3 HUFA or >90% purity HUFA fatty acids mixtures)

Cellular biomass of Thraustochytrium sp. S31 (ATCC 20888) was produced in a 10 liter fermenter in M-5/10 medium (see Example 9) at 27° C. The cells of this strain were harvested by centrifugation. Approximately 5 g of the cell paste was placed in the 350 mL stainless steel grinding chamber of a Bead-Beater bead mill which was filled ½ way with 0.5 mm glass beads. The remaining volumes of the chamber was filled with reagent grade MeOH and the cells homogenized for two 3 minute periods. During the bead mill operation, the stainless steel chamber was kept cold by an attached ice bath. The solution of broken cells was poured into a flask to which was added both chloroform and a 2M NaCl solution in water to bring the final solution to approximately 1:1:0.9 (chloroform:MeOH:water). The solution was then poured into a separatory funnel and shaken several times to help move the lipids into the chloroform fraction. After the solution was allowed to settle for several minutes, the chloroform fraction was collected into a flask, another portion of fresh chloroform added to the separatory funnel and the extraction repeated. This fraction of chloroform was then collected from the separatory funnel and the two chloroform portions combined. The chloroform was then removed (and recovered) by using a roto-vap rotary vacuum evaporation device operated at 40° C. A portion (300 mg) of the remaining lipids was removed and hydrolyzed for 6 hours at 60° C. (under nitrogen gas) in 50 mL of solution of methanolic NaOH (10 mL of 0.3N NaOH diluted to 100 mL with MeOH) in a 150 mL teflon lined screw capped bottle. The nonsaponifiable materials (sterols, hydrocarbons, etc.) were then removed by phase separating the solution with two 50 mL portions of petroleum either in a separatory funnel, discarding the ether fraction each time. The remaining solution was then acidified by addition of 3 mL of 6N HCl and the free fatty acids extracted with two 50 mL portions of petroleum ether. Five mL portion of the ether solution containing the free fatty acids was placed in three 13 mm×100 mm test tubes and the ether removed by blowing down the solution under a flow of nitrogen gas. Two mL portions of either petroleum ether, hexane or acetone were then added to one of tubes, which was then caped and placed in a solution of dry ice and ethanol (−72° to −74° C.) to allow the non-HUFA fatty acids to crystallize. When crystallization appeared complete, the culture tubes were placed in 50 mL polycarbonate centrifuge tubes that had been filled with finely powdered dry ice. These tubes were then placed in a refrigerated centrifuge at −10° C. and centrifuged for 3–5 minutes to 10,000 rpm. The supernatant was then quickly removed from each tube with a pasteur pipet and placed in a clean culture tube. The solvent was removed from the supernatants by blowing down under $N_2$. The fatty acids were then methylated in methanolic $H_2SO_4$ (4 mL $H_2SO_4$ in 96 mL MeoH) at 100° C. for 1 hr in teflon lined, screw capped tubes under $N_2$. The fatty acid methyl esters were then quantified by gas chromatography (HP 5890 gas chromatograph, Supelco SP 2330 column; column temp=200° C.; detector and injector temp=250° C.; carrier gas=nitrogen). The composition of the fatty acid mixtures obtained were: (ether) 93.1% HUFA's—23.4% C22:5n-6+ 69.7% 22:6n-3; (hexane) 91.5% HUFA's—66.8% 22:6n-3+ 22.1% 22:5n-6+2.6% 20:5n-3; (acetone) 90.0% HUFA's— 65.6% 22:6n-3+21.8n-6+2.6% 20:5n-3.

A fatty acid mixture containing >90% omega-3 HUFA's can be obtained by running the above process on harvested biomass of a strain of thraustochytrid such as 12B (ATCC 20890).

General Concluding Remarks

The following novel strains, isolated according to the method of the invention, were placed on deposit at the American Type Culture Collection (ATCC), Rockville, Md., as exemplars of the organisms disclosed and claimed herein.

| Strain | ATCC No. | Deposit Date |
| --- | --- | --- |
| Schizochytrium S31 | 20888 | 8/8/88 |
| Schizochytrium S8 | 20889 | 8/8/88 |
| Schizochytrium 12B | 20890 | 8/8/88 |
| Thraustochytrium U42-2 | 20891 | 8/8/88 |
| Schizochytrium 23B | 20892 | 8/8/88 |

The present invention, while disclosed in terms of specific organism strains, is intended to include all such methods and strains obtainable and useful according to the teachings disclosed herein, including all such substitutions, modification, and optimizations as would be available expedients to those of ordinary skill in the art.

REFERENCES

Ainsworth, G. C. (1973) "Introduction and keys to the higher taxa." In: *The Fungi. An Advanced Treatise*. Vol. 4B, G. C. Ainsworth et al. (eds.), Academic Press, New York, pp. 107.

Bahnweg, G. & Jackle, I. ( 1986 ) "A new approach to taxonomy of the Thraustochytriales and Lybrinthulales." In: *The Biology of Marine Fungi*, S. T. Moss (ed.), Cambridge University Press, London, pp. 131–140.

Barr, J. S. (1981) "The phylogenetic and taxonomic implications of flagellar rootlet morphology among zoosporic fungi." BioSystems 14:359–370.

Barr, J. S. (1983) "The zoosporic grouping of plant pathogens." In: *Zoosporic Plant Pathogens: a modern perspective*, S. T. Buczacki (ed.), Academic Press, pp. 43–83.

Bartnicki-Garcia, S. (1988) "The cell wall: a crucial structure in fungal evolution." In: *Evolutionary Biology of the Fungi*, A. D. M. Rayner et al. (eds.), Cambridge University Press, pp. 389–403.

CalBiochem Co. (1987). *Biochemical/Immunochemical Catalog*. Behring Diagnostics, La Jolla, Calif.

Cavalier-Smith, T. (1975) "The origin of nuclei and of eukaryotic cells." Nature 256:463–468.

Cavalier-Smith, T. (1983) "A 6-kingdom classification and a unified phylogeny." In: *Endocytobiology II: Intracellular Space as Oligogenetic System*, H. E. A. Schenk and W. Schwemmler (eds.), De Gruyter (Berlin), pp. 1027–1034.

Chamberlain, A. H. and Moss, S. T. (1988) "The thraustochytrids: a protist group with mixed affinities." BioSystems 21:341–349.

Cerda-Olmeda, E. & Lipson, E. (1987) Phycomyces, Cold Springs Harbor Laboratory, Cold Springs Harbor, N.Y.

Dick, M. W. (1973) "Saprolegniales." In: *The Fungi. An Advanced Treatise*, Vol. 4B, G. C. Ainsworth et al. (eds.), Academic Press, New York, pp. 113–144.

Ellenbogen, B. B. et al. (1969) "Polyunsaturated fatty acids of aquatic fungi: possible phylogenetic significance." Comp. Biochem. Physiol. 29:805–811.

Emerson, R. (1950) "Current trends of experimental research in the aquatic Phycomycetes." Ann. Rev. Micro. 4:169–200.

Erwin, J. (1973) "Comparative biochemistry of fatty acids in eukaryotic microorganisms." In: *Lipids and Biomembranes of Eukaryotic Microorganisms*, J. Erwin (ed.), Academic Press, New York, pp. 41–143.

Findlay, R. H. et al. (1986) "Biochemical indicators of the role of fungi and Thraustrochytrids in mangrove detrital systems." In: *The Biology of Marine Fungi*, S. T. Moss (ed.), Cambridge University Press, London, pp. 91–103.

Fuller, M. S. et al. (1964) "Isolation and pure culture of marine Phycomycetes." Mycologia 56:745–756.

Gellerman, J. L. & Schlenk, H. (1979) "Methyl-directed desaturation of arachidonic to eicosapentaenoic acid in the fungus, *Saprolegnia parasitica*." Biochem. Biophys. Acta 573:23–30.

Goldstein, S. (1963) "Development and nutrition of new species of *Thraustochytrium*." Am. J. Bot. 50:271–279.

Goldstein, S. et al. (1969) "Biology of a problematic marine fungus, Dermocystidium sp. II. Nutrition and repiration." Mycologia 61:468–72.

Hori, H. et al. (1980) Nucl. Acids Res. 8:5535–5539.

Hunter, J. E. (1987) "Fish oil and other omega-3 sources." J. Am. Oil Chem. Soc. 64:1592–1596.

Kates, M. (1986) *Techniques of Lipidology: Isolation, Analysis and Identification of Lipids*, Elsevier, Amsterdam.

Kazama, F. (1980) "The zoospore of *Schizoshytrium aggregatum*. Can J. Bot. 58:2434–2446.

Kyle, D. J. (1987) "Microalgae as a source of EPA-containing oils." Abstract of talk presented at World Conference for Fats & Oils, Hamburg, West Germany. J. Am. Oil Chem. Soc. 64:1251.

Leedale, G. (1974) "How many are the kingdoms of organisms." Taxon 23:261–270.

Lepage, G. and Roy, C. (1984) "Improved recovery of fatty acid through direct transesterification without prior extraction or purification." J. Lipid Res. 25:1391–1396.

Margulis, L. (1970) *Origin of Eukaryotic Cells*, Yale University Press, New Haven.

Margulis, L. and Sagan, D. (1985) "Order amidst animalcules: the Proctoctista kingdom and its undulipodiated cells." BioSystems 18:141–147.

Mannella, C. A. et al. (1987) "Interrelatedness of 5 S RNA sequences investigated by correspondence analysis." J. Mol. Evol. 24:228–235.

Moss, S. (1986) "Biology and phylogeny of the Labrinthulales and Thraustochytriales." In: *The Biology of Marine Fungi*, S. T. Moss (ed.), Cambridge University Press, London, pp. 105–130.

Perkins, F. O. (1976) "Fine structure of lower marine and estuarine fungi." In: *Recent Advances in marine Mycology*, E. B. Gareth Jones (ed.), Elek Science, pp. 279–312.

Pigot, G. M. (1989), "The need to improve omega-3 content of cultured fish," World Aquaculture 20:63–68)

Perkins, F. (1974) "Phylogenetic considerations of the problematic thraustochytriaceous-labrinthulid-Dermocystidium complex based on observations of fine structure." Veroff. Inst. Meeresforsch. Bremerh. Suppl. 5:45–63.

Pohl, P. and Zurheide, F. (1979) "Fatty acids and lipids of marine algae and the control of their biosynthesis by environmental factors." In: *Marine Algae in Pharmaceutical Science*, H. Hoppe et al. (eds.), W. de Gruyter, Berlin, pp. 473–524.

Poyton, R. (1970) "The characterization of *Hyallochlorella marina* gen. et sp. nov. a new colorless counterpart of Chlorella." J. Gert. Microbiol. 62:171–188.

Ryther, J. H. (1983) "Cultivation of macroscopic marine algae.I" In: *Solar Energy Research Institute Aquatic Species Program Review*. Proc. of the March 1983 Principal Investigators Meeting. SERI/CP-231-1946, pp. 79–88.

Sargent, J. et al. (1989), "The lipids," in *Fish Nutrition, Second Edition*, J. Halver (ed.), Academic Press, pp. 153–218.

Schlenk, H. (1954) "Urea inclusion compounds of fatty acids." Prog. Chem. Fats and Other Lipids 2:243:267.

Schneider, J. (1976) "Cultivation of Microorganisms. Section 3.2: Fungi." In: *Marine Ecology*, Vol. 3, Part 1. *Cultivation*, O. Kinne (ed.), Wiley Interscience.

Sigma Chemical Co. (1988). Catalog: Biochemical and Organic Compounds for Research. Sigma Chemical Co., St. Louis, Miss.

Simopoulos, A. P. et al. (1986) *Health Effects of Polyunsaturated Fatty Acids in Seafoods*, Academic Press, New York.

Sorokin, C. (1973) "Growth measurements: dry weight packed cell volume, and optical density." In: *Handbook of Phycological Methods: Culture Methods and Growth Measurements*, J. R. Stein (ed.), Cambridge University press, Cambridge, pp. 321–343.

Sparrow, F. K. (1960) *Aquatic Phycomycetes*. University of Michigan Press, Ann Arbor, pp. 37–38.

Wassef, M. (1977) "Fungal lipids." Adv. Lipid Res. 15:159–232.

Weete, J. D. (1980) *Lipid Biochemistry of Fungi and Other Organisms*. Plenum Press, New York.

Yamada, H. et al. (1987) "Production of arachidonic acid and eicosapentaenoic acid by microorganisms." Abstract of talk presented at Wold Conference for Fats & Oils, Hamburg, West Germany. J. Am Oil. Chem. Soc. 64:1254.

What is claimed is:

1. A food product, comprising the flesh of an animal, wherein said animal is raised by feeding said animal material selected from the group consisting of Thraustochytriales, omega-3 highly unsaturated fatty acids extracted from Thraustochytriales, and mixtures thereof in an amount effective to increase the content of omega-3 highly unsaturated fatty acids in said animal.

2. A food product, comprising an egg, wherein said egg is from poultry raised by feeding said poultry material selected from the group consisting of Thraustochytriales, omega-3 highly unsaturated fatty acids extracted from Thraustochytriales, and mixtures thereof in an amount effective to increase the content of omega-3 highly unsaturated fatty acids in said animal.

3. A food product, as claimed in claim 1, wherein said animal is poultry.

4. A food product, as claimed in claim 1, wherein said animal is a chicken.

5. A food product, as claimed in claim 1, wherein said animal is cattle.

6. A food product, as claimed in claim 1, wherein said animal is seafood.

7. A food product, as claimed in claim 6, wherein said seafood is selected from the group consisting of fish, shrimp, shellfish, and mixtures thereof.

8. A food product, as claimed in claim 1, wherein said animal is swine.

* * * * *